United States Patent
Hernández Cabanillas et al.

(10) Patent No.: US 11,584,710 B2
(45) Date of Patent: Feb. 21, 2023

(54) COMPOUNDS FOR TREATING INFECTIONS

(71) Applicant: HORITZONTS TECNOLOGICS HUNGARY KORLÁTOLT FELELOSSÉGU TÁRSASÁG, Budapest (HU)

(72) Inventors: Alfredo Hernández Cabanillas, Cáceres (ES); Santiago Maderuelo Corral, Madrid (ES); Montserrat Ortega Doménech, Madrid (ES); Diego Fernando Rosero Valencia, Madrid (ES); Ángel Rumbero Sánchez, Madrid (ES); Victor Tena Pérez, Villanueva de la Serena (ES)

(73) Assignee: HORITZONTS TECNOLOGICS HUNGARY KORLÁTOLT FELELOSSÉGU TÁRSASÁG, Budapest (HU)

( * ) Notice: Subject to any disclaimer, the term of this patent is extended or adjusted under 35 U.S.C. 154(b) by 129 days.

(21) Appl. No.: 16/635,688

(22) PCT Filed: Jul. 31, 2018

(86) PCT No.: PCT/EP2018/070700
§ 371 (c)(1),
(2) Date: Jan. 31, 2020

(87) PCT Pub. No.: WO2019/025426
PCT Pub. Date: Feb. 7, 2019

(65) Prior Publication Data
US 2021/0155578 A1    May 27, 2021

(30) Foreign Application Priority Data
Jul. 31, 2017  (EP) .................................... 17382521

(51) Int. Cl.
| C07C 243/34 | (2006.01) |
| A61P 31/10 | (2006.01) |
| C07C 243/28 | (2006.01) |
| C07C 259/06 | (2006.01) |

(52) U.S. Cl.
CPC ............ *C07C 243/34* (2013.01); *A61P 31/10* (2018.01); *C07C 243/28* (2013.01); *C07C 259/06* (2013.01)

(58) Field of Classification Search
CPC ... C07C 243/28; C07C 243/34; C07C 259/06; A61P 31/00
See application file for complete search history.

(56) References Cited

U.S. PATENT DOCUMENTS

| 2,706,732 A | 4/1955 | Duschinsky |
| 2,758,050 A | 8/1956 | Hackmann |

FOREIGN PATENT DOCUMENTS

| DE | 22 23 936 | 12/1973 |
| DE | 24 36 544 | 2/1975 |
| EP | 0 217 310 A2 | 4/1987 |
| JP | 09090537 A * | 4/1997 ............... G03C 1/06 |
| WO | 05/000281 A2 | 1/2005 |
| WO | 09/073620 A2 | 6/2009 |

OTHER PUBLICATIONS

Heinisch, V.L. et al., "Virushemmung in vitro durch Semioxamazid-Derivate", 1968, vol. 18, No. 10, pp. 1324-1328 2009.
López-Alvarado, P. et al., "Versatile synthesis of malonamic acid derivatives from a β-ketothioester", Tetrahedron Letters, 2001, vol. 42, pp. 4479-4482.
Roberts, D.A. et al., "1, 2, 4-Triazolo [4,3-a] pyrazine Derivatives with Human Renin Inhibitory Activity. 1. Synthesis and Biological Properties of Alkyl Alcohol and Statine Derivatives", Journal of Medicinal Chemistry, 1990, vol. 33, No. 9, pp. 2376-2334.
Sechi, M. et al., "Design and Synthesis of Bis-amide and Hydrazide-containing Derivatives of Malonic Acid as Potential HIV-1 Integrase Inhibitor", Molecules, 2003, vol. 13, pp. 2442-2461.
Database CAPLUS, database accession No. 1906:534.
Database CAPLUS, database accession No. 1949:30272.
Database CAPLUS, database accession No. 2010:489627.
International Search Report issued by the International Searching Authority (ISA/O.E.P.M.) dated Oct. 2, 2013 in connection with International Application No. PCT/ES2018/070700.
Thiele, J. and Schleussner K. , "Ueber Diamidophenylosotriazol", Justus Liebigs Annalen der Chemie, 1897, vol. 295, No. 2, pp. 129-172, including English language translation of part thereof.

* cited by examiner

*Primary Examiner* — Theodore R. Howell
(74) *Attorney, Agent, or Firm* — Gary J. Gershik

(57) ABSTRACT

The invention relates to hydrazide compounds and their use in medicine, particularly in treating and/or preventing infections caused by a fungus.

4 Claims, 12 Drawing Sheets

COMPOUNDS FOR TREATING INFECTIONS

RELATED APPLICATIONS

This application is a § 371 national stage of PCT International Application No. PCT/EP2018/070700, filed Jul. 31, 2018, claiming priority of European Patent Application No. 17 382 521.7, filed Jul. 31, 2017, the contents of each of which are hereby incorporated by reference into this application.

TECHNICAL FIELD OF INVENTION

The present invention relates to new compounds and their use in medicine, particularly as agents able to treat and/or prevent infections caused by fungus.

BACKGROUND OF INVENTION

The discovery of penicillin ushered in the "antibiotic era" and the ability to cure infections which were previously often fatal.

The advantages offered by antibiotics in the treatment of infectious diseases are compromised due to the increase in the number of antibiotic-resistant bacterial strains. Antimicrobial resistance makes it difficult and more expensive to treat a variety of common infections, causing delays in effective treatment, or in worst cases, inability to provide appropriate therapy. The predictable consequences of resistance are increased morbidity, prolonged illness, a greater risk of complications, and higher mortality rates. The economic burden includes loss of productivity (loss in income, diminished worker productivity, time spent by family) and increased cost of diagnostics and treatment (consultation, infrastructure, screening, cost of equipment, drugs . . . ). It has been reported that every year 25000 patients die in the European Union from a bacterial infection which is multi-resistant to the presently existing drugs.

The problem of resistance also covers the major pathogenic fungi and yeasts, encompassing fungal infections, with ever increasing due to their behavior as typical opportunistic. To date, fungal infections continue to be an important cause of morbidity and mortality very high, and may reach up to 100% in some disseminated infections.

In addition, although already exists in the market more than 20 anti-HIV drugs, there is a need of new types of antiviral drugs to palliate the new resistances.

The requirements for new antibiotic, antifungal and antiviral molecules are in accordance with current problem of drug and multidrug resistance. It is an increasingly serious threat to global public health that drug resistance is present in all parts of the world. There are now very few effective drugs available to treat recently emerged multidrug resistant infections.

There is still a need in the state of the art to identify suitable, effective new compounds for the prevention and/or treatment of infections.

SUMMARY OF THE INVENTION

In a first aspect, the invention relates to a compound of formula (I):

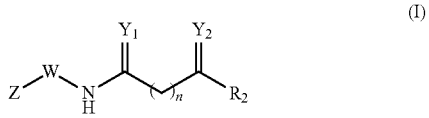

or a pharmaceutically acceptable salt, stereoisomer or solvate thereof,
wherein
$Y_1=O$;
$Y_2=O$;
$W=NH$;
$n=0, 1$;
$R_2=NHR_4$, wherein $R_4$ is selected from the group consisting of, OH, $-NH_2$, $-NH-CH_3$ and $-NR_aR_b$, wherein $R_a$ and $R_b$ are independently selected $C_{1-6}$ alkyl groups or aryl groups;
$Z$=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, $-SH$, $-OR_5$, $-SR_5$, OH, $NO_2$, $C(O)NH-R_5$, $-C(O)OR_5$, $-OC(O)R_5$, $CF_3$, CN, $-NH_2$, NHOH, $-NH-NH_2$, $-NH-CH_3$ and $-NR_6R_7$, wherein $R_5$ is $C_{1-6}$ alkyl, aryl or hydrogen, wherein $R_6$ and $R_7$ are independently selected from $C_{1-6}$ alkyl, aryl, $-C(O)R_5$, $-OC(O)R_5$, or $-C(O)OR_5$, with the proviso that when $Y_1=Y_2=O$; $n=0$; $R_2=NHNH_2$ and W is NH then Z is not a group selected from the group consisting of a pyridine group, and a phenyl group wherein the phenyl group is optionally substituted with methyl, halogen, $NO_2$ or $OCH_3$ group.

In a second aspect, the invention relates to a compound of formula (II):

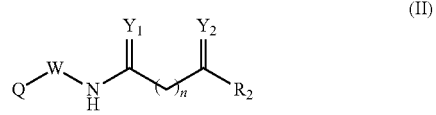

or a pharmaceutically acceptable salt, stereoisomer or solvate thereof,
wherein
$Y_1=O$;
$Y_2=O$;
$W=NH$;
$n=0, 1$;
$R_2=NHR_4$, and wherein $R_4$ is selected from the group consisting of OH, $-NH_2$, $-NH-CH_3$ and $-NR_aR_b$, wherein $R_a$ and $R_b$ are independently selected $C_{1-6}$ alkyl groups or aryl groups;
Q is selected from the group consisting of:
a) 1-pyridine, 2-pyridine, 3-pyridine,
b) phenyl optionally substituted with one or more groups independently selected from the group consisting of $C_{1-8}$ alkyl, $C_{2-8}$ alkenyl, halogen, $-SH$, $-OR_5$, $-SR_5$, OH, $NO_2$, $C(O)NH-R_5$, $-C(O)OR_5$, $-OC(O)R_5$, $CF_3$, CN, $-NH_2$, $-NHOH$, $-NH-NH_2$, $-NH-CH_3$ and $-NR_6R_7$, wherein R₅ is C_{1-6} alkyl, aryl, or hydrogen, wherein R₆ and R₇ are independently selected from C_{1-6} alkyl groups, aryl groups, —C(O)R₅—, —OC(O)R₅, or —C(O)OR₅—, c) 5-6 membered aromatic ring having one or more heteroatoms selected from the group consisting of N, S, and O and being optionally substituted with one or more groups independently selected from the group consisting of:
C_{1-8} alkyl, linear or branched C_{1-8} alkenyl, C_{5-6} cycloalkyl,
phenyl as defined in b),
5-6 membered aromatic ring group having one or more heteroatoms selected from N, S, and O,
halogen,
(C_{1-6}alkyl)OCH₂—,
C_{1-6} alkoxy,
NR_aR_b, wherein R_a and R_b are independently selected from C_{1-6} alkyl groups or aryl groups, and
NHC(O)R₅—, —C(O)NH—R₅, —OC(O)R₅, and —C(O)OR₅—, wherein R₅ is C_{1-6} alkyl, aryl or hydrogen, and d) a fused bicyclic ring containing at least one phenyl group and a C_{5-6} aromatic heterocyclic group having one or more heteroatoms selected from N, S, and O, wherein the phenyl group of said fused bicyclic ring is optionally substituted with one or more groups independently selected from
C_{1-8} alkyl, linear or branched C_{1-8} alkenyl, C_{5-6} cycloalkyl,
phenyl as defined in b),
5-6 membered aromatic ring group as defined in c),
halogen,
(C_{1-6}alkyl)OCH₂—,
C_{1-6}alkoxy,
OH, —SH or —SR₅ wherein R₅ is C_{1-6} alkyl, aryl or hydrogen,
—NR₆R₇, wherein R₆ and R₇ are independently selected from C_{1-6} alkyl groups, aryl groups, —C(O)R₅, —OC(O)R₅, or —C(O)OR₅, wherein R₅ is C_{1-6} alkyl, aryl, or hydrogen, and
NHC(O)R₅—, —C(O)NH—R₅, —OC(O)R₅, and —C(O)OR₅—, wherein R₅ is C_{1-6} alkyl, aryl or hydrogen, with the proviso that when Y₁=Y₂=O; n=0; R₂=NHNH₂ and W is NH then Q is not a phenyl group, or a pharmaceutical composition comprising said compound and a pharmaceutically acceptable excipient for use in medicine.

In a third aspect, the invention relates to a pharmaceutical composition comprising a compound of formula (II)

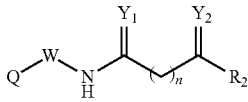

(II)

or a pharmaceutically acceptable salt, stereoisomer or solvate thereof,
wherein
Y₁=O;
Y₂=O;
W=NH
n=0, 1;

R₂=NHR₄, wherein R₄ is selected from, OH, —NH₂, —NH—CH₃ and —NR_aR_b, wherein R_a and R_b are independently selected C_{1-6} alkyl groups or aryl groups, Q is selected from a group consisting of:

a) 1-pyridine, 2-pyridine, 3-pyridine, b) phenyl optionally substituted with one or more groups independently selected from C_{1-8} alkyl, C_{2-8} alkenyl, halogen, —SH, —OR₅, —SR₅, OH NO₂, C(O)NH—R₅, —C(O)OR₅, —OC(O)R₅, CF₃, CN, NH₂, —NHOH, —NH—NH₂, —NH—CH₃ and —NR₆R₇, wherein R₅ is C_{1-6} alkyl, aryl, or hydrogen, wherein R₆ and R₇ are independently selected C_{1-6} alkyl groups, aryl groups, —C(O)R₅, —OC(O)R₅, or —C(O)OR₅—, c) 5-6 membered aromatic ring having one or more heteroatoms selected from N, S, and O and being optionally substituted with one or more groups independently selected from:
C_{1-8} alkyl, linear or branched C_{1-8} alkenyl, C_{5-6} cycloalkyl,
phenyl as defined in b),
5-6 membered aromatic ring group having one or more heteroatoms selected from N, S, and O,
halogen.
(C_{1-6}alkyl)OCH₂—,
C_{1-6} alkoxy,
NR_aR_b, wherein R_a and R_b are independently selected from C_{1-6} alkyl groups or aryl groups, and
NHC(O)R₅—, —C(O)NH—R₅, —OC(O)R₅, and —C(O)OR₅—, wherein R₅ is C_{1-6} alkyl, aryl or hydrogen, and d) a fused bicyclic ring containing at least one phenyl group and a C_{5-6} aromatic heterocyclic group having one or more heteroatoms selected from N, S, and O, wherein the phenyl group of said fused bicyclic ring is optionally substituted with one or more groups independently selected from
C_{1-8} alkyl, linear or branched C_{1-8} alkenyl, C_{5-6} cycloalkyl,
phenyl as defined in b),
5-6 membered aromatic ring group as defined in c),
halogen,
(C_{1-6}alkyl)OCH₂—,
C_{1-6} alkoxy,
OH, —SH or —SR₅ wherein R₅ is C_{1-6} alkyl, aryl or hydrogen,
NR₆R₇, wherein R₆ and R₇ are independently selected from C_{1-6} alkyl groups, aryl groups, C(O)R₅, —OC(O)R₅, or —C(O)OR₅, wherein R₅ is C_{1-6} alkyl, aryl or hydrogen, and
NHC(O)R₅—, —C(O)NH—R₅, —OC(O)R₅, or —C(O)OR₅—, wherein R₅ is C_{1-6} alkyl, aryl, or hydrogen,
and a pharmaceutically acceptable excipient for use in the prevention and/or treatment of an infection caused by fungus.

*terreus* (B); Compound 150 µg in *C. albicans* (C) and *A. terreus* (D). Control: Ketoconazole 50 µg, bottom spot of each figure.

Figure 3:
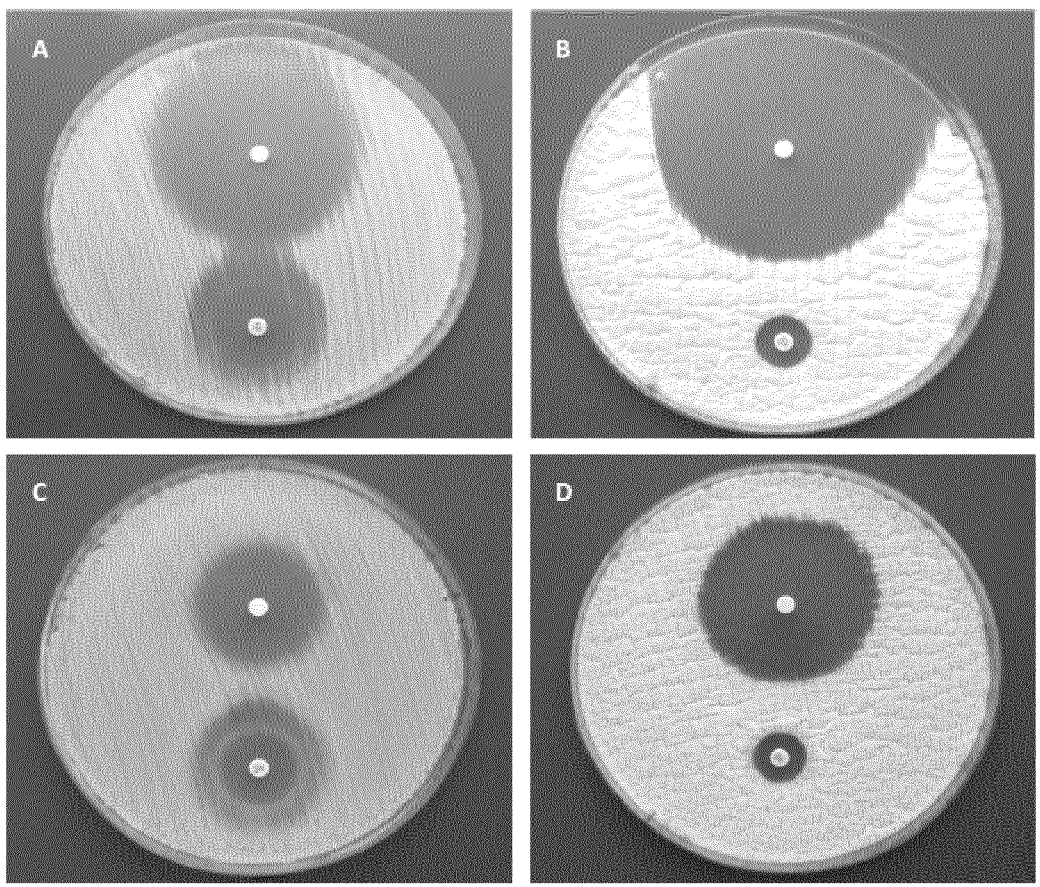

FIG. 3. Antifungal activity of the compound MSG-193. Compound 500 µg in *C. albicans* (A) and *A. niger* (B); Compound 150 µg in *C. albicans* (C) and *A. niger* (D). Control: Ketoconazole 50 µg, bottom spot of each figure.

Figure 4:
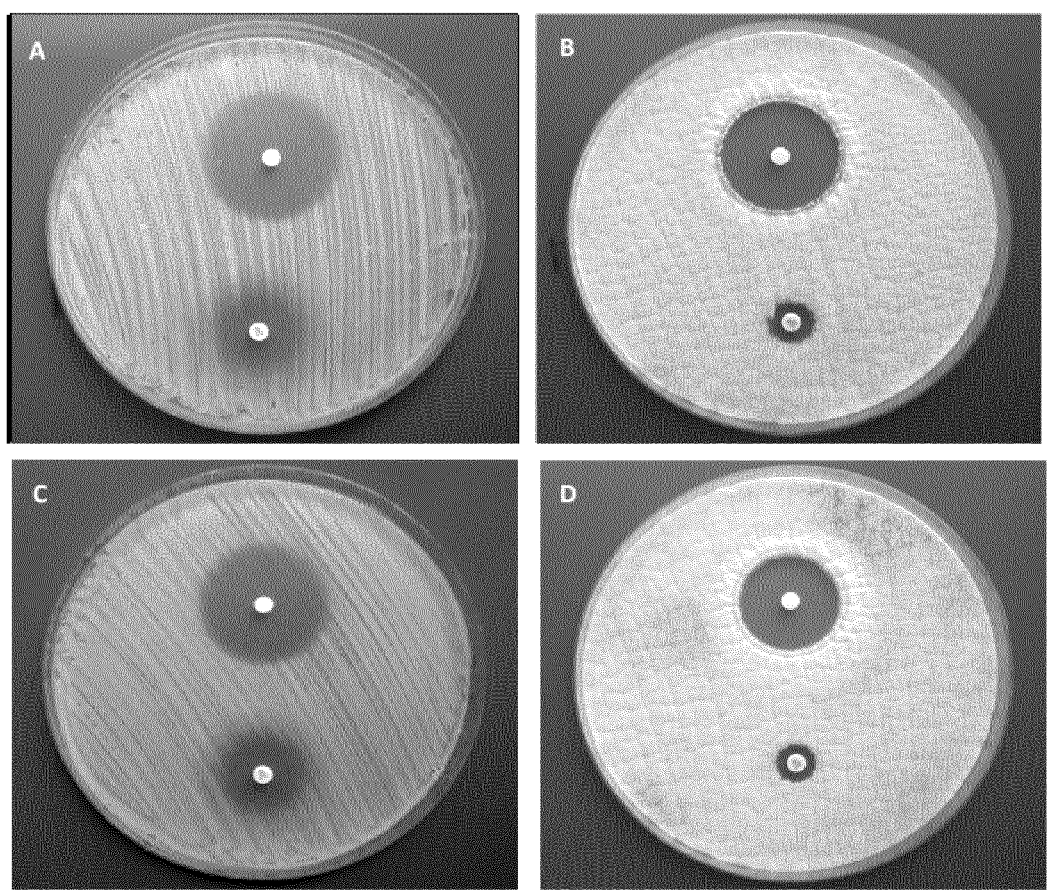

FIG. 4. Antifungal activity of the compound MSG-210. Compound 500 µg in *C. albicans* (A) and *A. niger* (B); Compound 150 µg in *C. albicans* (C) and *A. niger* (D) Control: Clotrimazole 10 µg bottom spot of each figure.

Figure 5:
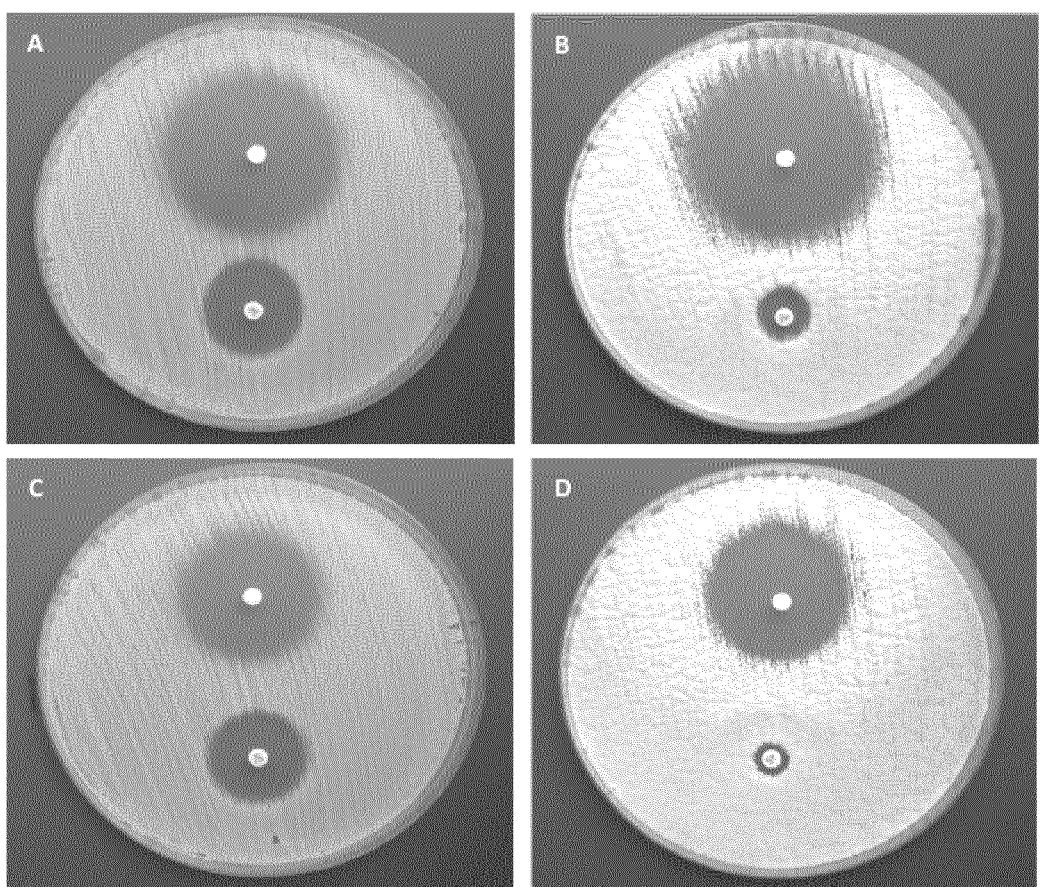

FIG. 5. Antifungal activity of the compound MSG-214. Compound 500 µg in *C. lusitaniae* (A) and *A. niger* (B); Compound 150 µg in *C. lusitaniae* (C) and *A. niger* (D). Control: Clotrimazole 10 µg bottom spot of each figure.

Figure 6:
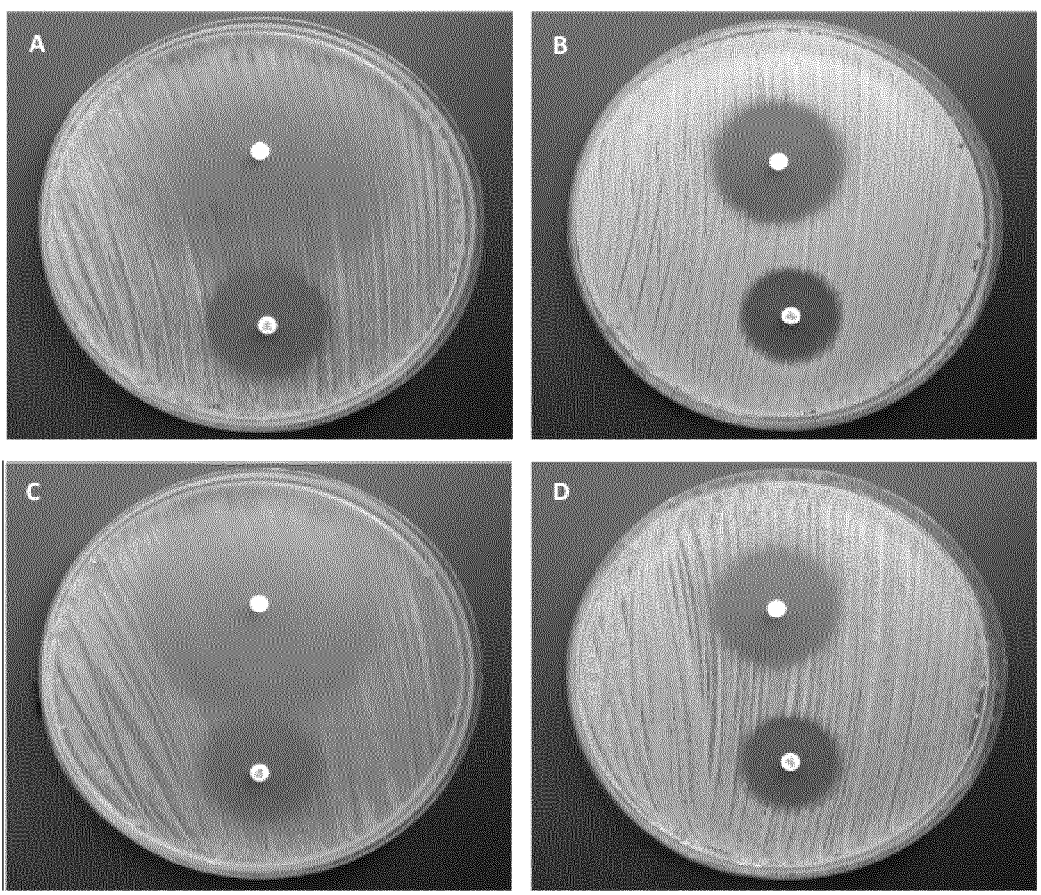

FIG. 6. Antifungal activity of the compound MSG-216. Compound 500 µg in *C. albicans* (A) and *C. lusitaniae* (B); Compound 150 µg in *C. albicans* (C) and *C. lusitaniae* (D). Control: Clotrimazole 10 µg bottom spot of each figure.

Figure 7:
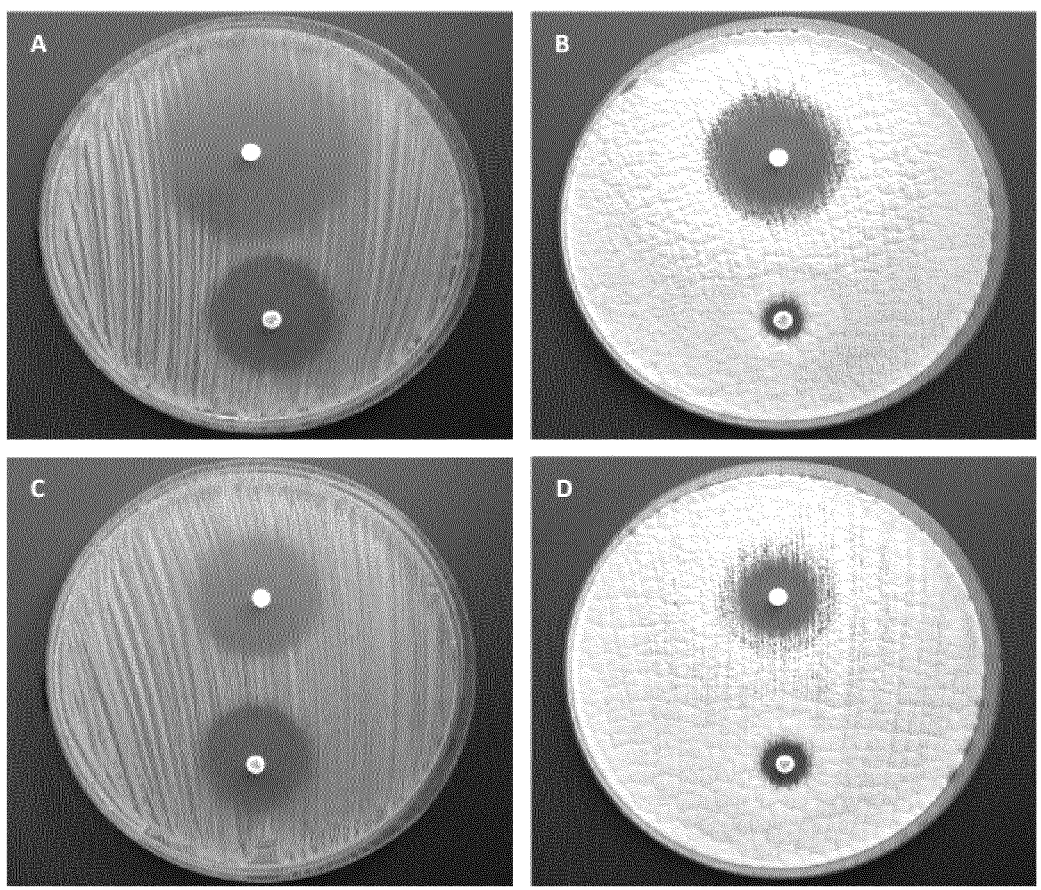

FIG. 7. Antifungal activity of the compound MSG-218. Compound 500 µg in *C. albicans* (A) and *A. niger* (B); Compound 150 µg in *C. albicans* (C) and *A. niger* (D). Control: Clotrimazole 10 µg bottom spot of each figure.

Figure 8:
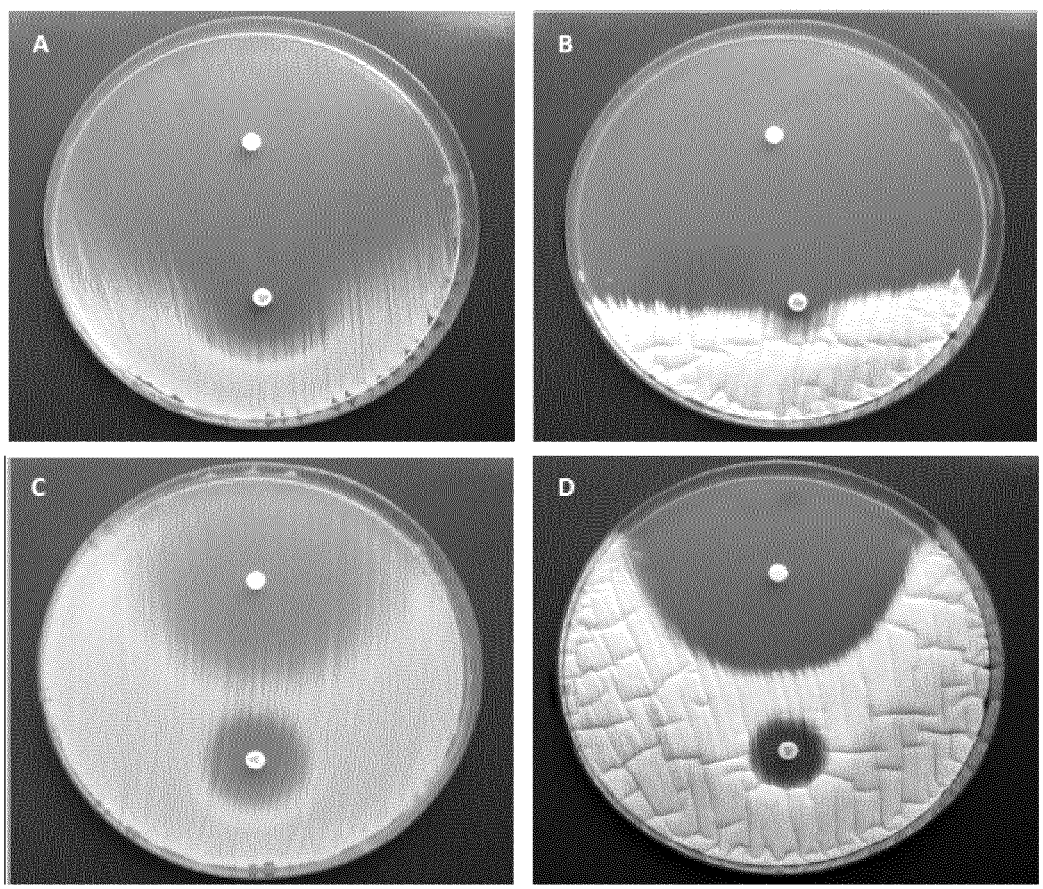

FIG. 8. Antifungal activity of the compound MSG-227. Compound 500 µg in *C. guillermondii* (A) and *A. terreus* (B); Compound 150 µg in *C. guillermondii* (C) and *A. terreus* (D). Control: Clotrimazole 10 µg bottom spot of each figure.

Figure 9:
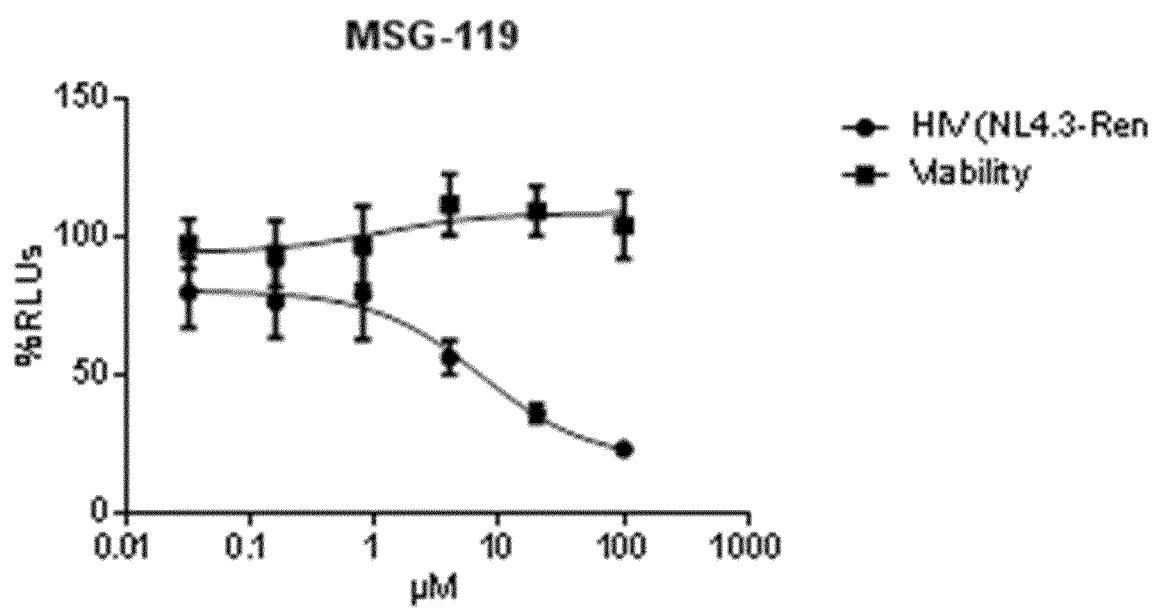

FIG. 9. Anti-HIV activity of the compound MSG-119

DETAILED DESCRIPTION OF THE INVENTION

The inventors have identified new compounds having antibiotic antifungal, and antiviral activity as shown in Examples 1-5.

Compounds of the Invention

In a first aspect, the invention relates to a compound of formula (I):

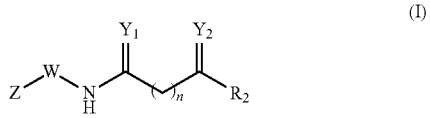

or a pharmaceutically acceptable salt, stereoisomer or solvate thereof,
wherein
$Y_1$=O, NH;
$Y_2$=O, NH;
W=O, NH;
n=0, 1;
$R_2$=$OR_3$ or $NHR_4$, wherein $R_3$ is selected from the group consisting of H, $C_1$-$C_6$ alkyl, and aryl; and wherein $R_4$ is selected from the group consisting of H, OH, $C_1$-$C_6$ alkyl, aryl groups, —$NH_2$, —NH—$CH_3$ and —$NR_aR_b$, wherein $R_a$ and $R_b$ are independently selected $C_{1-6}$ alkyl groups or aryl groups;
Z=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —NH—$NH_2$, —NH—$CH_3$ and —$NR_6R_7$, wherein $R_5$ is $C_{1-6}$ alkyl, aryl or hydrogen, wherein $R_6$ and $R_7$ are independently selected from $C_{1-6}$ alkyl, aryl, —C(O)$R_5$, —OC(O)$R_5$, or —C(O)$OR_5$, with the proviso that when $Y_1$=$Y_2$=O; n=0; $R_2$=$NHNH_2$ and W is NH then Z is not a group selected from the group consisting of a pyridine group, and a phenyl group wherein the phenyl group is optionally substituted with methyl, halogen, $NO_2$ or $OCH_3$ group.

In a preferred embodiment of the compound of the invention is the compound of formula (I) wherein $Y_1$=O; $Y_2$=O; W=NH; n=0, 1 and $R_2$=$NHR_4$, wherein $R_4$ is selected from the group consisting of OH, —$NH_2$, —NH—$CH_3$ and —$NR_aR_b$, wherein $R_a$ and $R_b$ are independently selected $C_{1-6}$ alkyl groups and Z=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —NH—$NH_2$, —NH—$CH_3$ and —$NR_6R_7$, wherein $R_5$ is $C_{1-6}$ alkyl, aryl or hydrogen, wherein $R_6$ and $R_7$ are independently selected from $C_{1-6}$ alkyl, aryl, —C(O)$R_5$, —OC(O)$R_5$, or —C(O)$OR_5$.

"Alkyl" refers to a straight or branched hydrocarbon chain radical consisting of carbon and hydrogen atoms, containing no unsaturation, and which is attached to the rest of the molecule by a single bond. Alkyl groups having 1, 2, 3, 4, 5, 6, or 7 carbon atoms are particularly preferred. Methyl, ethyl, n-propyl, iso-propyl and butyl, pentyl, hexyl, heptyl, including n-butyl, tert-butyl, sec-butyl and iso-butyl are particularly preferred alkyl groups. As used herein, the term alkyl, unless otherwise stated, refers to both cyclic and noncyclic groups, although cyclic groups will comprise at least three carbon ring members, such as cyclopropyl or cyclohexyl.

The term "$C_{1-8}$ alkyl" refers to a linear or branched hydrocarbon chain radical consisting of carbon and hydrogen atoms, containing no insaturation, having between 1 and 8, preferably between 1 and 6 ("$C_{1-6}$ alkyl"), carbon atoms and which is attached to the rest of the molecule by a single bond, including for example and in a non-limiting sense, methyl, ethyl, n-propyl, i-propyl, n-butyl, t-butyl, n-pentyl, n-hexyl, t-hexyl, n-heptyl, t-heptyl, etc.

The term "$C_{1-6}$ alkyl" refers to a linear or branched hydrocarbon chain radical consisting of carbon and hydrogen atoms, containing no insaturation, having between 1 and 6, preferably between 1 and 3 ("$C_{1-3}$ alkyl"), carbon atoms and which is attached to the rest of the molecule by a single bond, including for example and in a non-limiting sense, methyl, ethyl, n-propyl, i-propyl, n-butyl, t-butyl, n-pentyl, etc. Preferably "alkyl" refers to methyl or ethyl.

"Alkenyl" refers to a straight or branched hydrocarbon chain radical consisting of carbon and hydrogen atoms, containing one or more unsaturated bonds, and which is attached to the rest of the molecule by a single bond. The term "$C_{1-8}$ alkenyl" refers to a linear or branched hydrocarbon chain radical consisting of carbon and hydrogen atoms, containing one or more unsaturated bonds, having between 1 and 8 carbon atoms, preferably between 2 and 8 ("$C_{2-8}$ alkenyl"), or more preferably between 2 and 6 ("$C_{2-6}$ alkenyl") carbon atoms and which is attached to the rest of the molecule by a single bond. Examples of alkenyl groups include ethenyl, propenyl, allyl, butenyl, 1-methyl-2-buten-1-yl, and the like.

"Aryl" as used herein relates to single and multiple ring compounds, including multiple ring compounds that contain separate and/or fused aryl groups. Typical aryl groups contain from 1 to 3 separated and/or fused rings and from 6 to about 18 carbon ring atoms. In a particular embodiment the aryl group is a fused bicyclic aromatic ring wherein two aromatic rings are fused.

Preferably aryl groups contain from 6 to about 10 carbon ring atoms. Specially preferred aryl groups include phenyl, naphthyl, biphenyl, phenanthryl, anthracyl and the like. The term includes but is not limited to, phenyl, naphthyl, tetrahydronaphthyl, indanyl, indenyl, and the like. In a preferred embodiment the aryl is phenyl.

The term "$C_{6-12}$ aryl" refers to an aromatic group having between 6 and 12, preferably between 6 and 10 ("$C_{6-10}$ aryl"), more preferably 6 or 10 carbon atoms, comprising 1 or 2 aromatic nuclei, bound by means of a carbon-carbon bond or fused, including for example and in a non-limiting sense, phenyl, naphthyl, diphenyl, etc. Preferably "aryl" refers to phenyl.

The term "aromatic heterocyclic ring" refers to an aromatic ring containing one or more heteroatoms in the structure. Preferably the heteroatom or heteroatoms in the aromatic heterocyclic ring are selected from N, S and O. Preferably, the aromatic heterocyclic ring is selected from 1-pyridine, 2-pyridine and 3-pyridine.

The terms "halogen", "halo" or "hal" refer to bromo, chloro, iodo or fluoro.

In a preferred embodiment, $R_2$ is NH—$NH_2$ or n is 1 and $Y_1$=$Y_2$=O. In another preferred embodiment, $R_2$ is NH—$NH_2$ and n is 1 and $Y_1$=$Y_2$=O.

In another preferred embodiment, Z is a phenyl group optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —$NHNH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$—.

In another preferred embodiment, the compound according to the invention is a compound of formula (III)

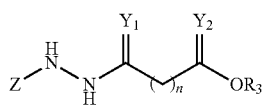

(III)

wherein
$Y_1$=O, NH;
$Y_2$=O, NH;
n=0, 1;
$R_3$ is selected from H and $C_1$-$C_6$ alkyl, and
Z=1-pyridine, 2-pyridine, 3-pyridine or phenyl optionally substituted with one or more groups independently selected from $C_{1-8}$ alkyl, $C_{2-8}$ alkenyl, halogen, —SH, —$OR_5$, —$NO_2$, $C_{1-6}$ alkoxy, C(O)NH—$R_5$, —C(O)$OR_5$, —OC(O)$R_5$, —$CF_3$, —CN, —$NH_2$, —NH—$CH_3$ and —$NR_6R_7$, wherein $R_5$ is $C_{1-6}$ alkyl, aryl or hydrogen and wherein $R_6$ and $R_7$ are independently selected from $C_{1-6}$ alkyl groups, aryl groups, —C(O)$R_5$, —NHC(O)$R_5$—, —C(O)NH—$R_5$, —OC(O)$R_5$, and —C(O)$OR_5$—.

In another preferred embodiment, the compound according to the invention is a compound of formula (IV)

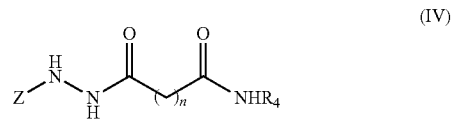

(IV)

wherein
n=0, 1;
$R_4$ is selected from H, OH, and $NH_2$,
Z=1-pyridine, 2-pyridine, 3-pyridine or phenyl, wherein the phenyl is optionally substituted with one or more groups independently selected from $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —NH—$NH_2$, —NH—$CH_3$ and —$NR_6R_7$, wherein $R_5$ is $C_{1-6}$ alkyl, aryl or hydrogen, wherein $R_6$ and $R_7$ are independently selected from $C_{1-6}$ alkyl groups, aryl groups, —C(O)$R_5$, —OC(O)$R_5$, or —C(O)$OR_5$,
with the proviso that when $Y_1$=$Y_2$=O; n=0 and $R_4$ is $NH_2$ then Z is not a group selected from a pyridine group, or a phenyl group optionally substituted with methyl, halogen, $NO_2$ and $OCH_3$ group.

In another preferred embodiment, the compound according to the invention is the compound of formula (IV) wherein $R_4$ is $NH_2$.

In another preferred embodiment, the compound according to the invention is a compound of formula (V):

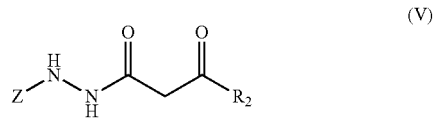

(V)

wherein
$R_2$=$OR_3$ or $NHR_4$, wherein $R_3$ is selected from H, $C_1$-$C_6$ alkyl and aryl, and wherein $R_4$ is selected from H, OH, $C_1$-$C_6$ alkyl, aryl groups, —$N_2$, —NH—$CH_3$ and —$NR_aR_b$, wherein $R_a$ and $R_b$ are independently selected $C_{1-6}$ alkyl groups or aryl groups.
Z=1-pyridine, 2-pyridine, 3-pyridine or phenyl optionally substituted with one or more groups independently selected from $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —$NH_2NH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

In a preferred embodiment, the compound of the invention is a compound of formula (V) wherein $R_2$ is $NHR_4$, wherein $R_4$ is selected from OH, —$NH_2$, —NH—$CH_3$ and —$NR_aR_b$, wherein $R_a$ and $R_b$ are independently selected $C_{1-6}$ alkyl groups.

In a more preferred embodiment, the compound according to the invention is a compound of formula (VI):

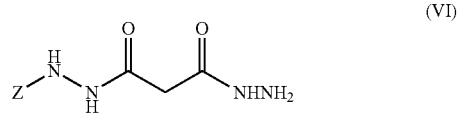

(VI)

wherein
Z=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —$NH_2NH_2$, —NH—$CH_3$ and —$NR_6R_7$, wherein $R_4$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

In another preferred embodiment, the compound according to the invention is a compound of formula (VII):

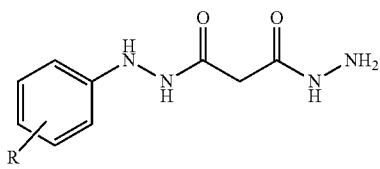

(VII)

wherein the phenyl group is optionally substituted with one or more groups independently selected from $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —$NH_2NH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

In a more referred embodiment, the compound of the invention is

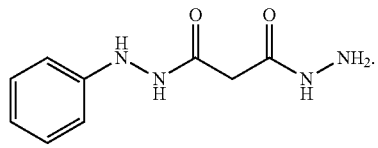

(Ia) MSG187

In another preferred embodiment, the compound of the invention is

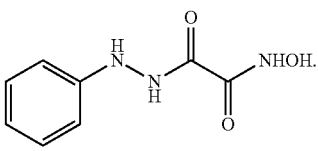

(Ib) MSG158

In another preferred embodiment, the compound of the invention is

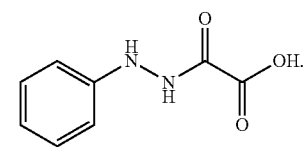

(Ic) MSG160

In another preferred embodiment, the compound of the invention is

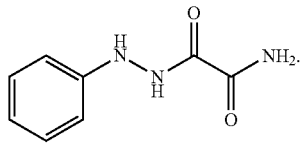

(Id) MSG159

In another preferred embodiment, the compound of the invention is

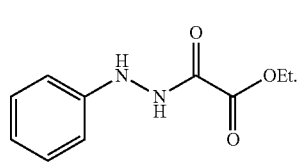

(Ie) MSG156

In another preferred embodiment, the compound of the invention is

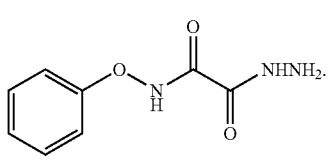

(If) MSG196

In another preferred embodiment, the compound of the invention is

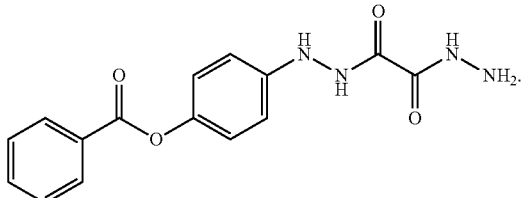

(Ig) MSG231

In another preferred embodiment, the compound is:

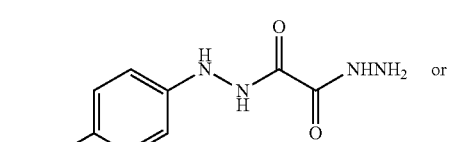

(IIg) MSG223

(IIm) MSG161

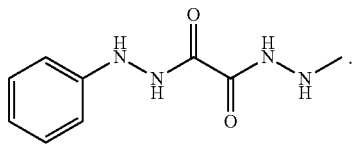

The invention also relates to a pharmaceutically acceptable salt, stereoisomer or solvate of a compound of the invention.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to "pharmacologically acceptable salts" or "pharmaceutically acceptable salts".

The term "physiologically acceptable salt" or "pharmaceutically acceptable salt" is understood in particular, in the context of this invention, as a salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, non-aqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. Since hydroxytyrosol has three hydroxyl groups, alkali addition salts are particularly preferred such as Na+ and NX4+ (wherein X is independently selected from H or a C1-C4 alkyl group).

For those persons skilled in the art, it will be evident that the scope of the present invention also includes salts which are not pharmaceutically acceptable as possible means for obtaining pharmaceutically acceptable salts.

Any compound referred to herein is intended to represent such specific compound as well as certain variations or forms. The compounds of the present invention represented by the above described formulas include stereoisomers. The term "stereoisomer" as used herein includes any enantiomer, diastereomer or geometric isomer (E/Z) of such compound.

In particular, compounds referred to herein may have asymmetric centres and therefore exist in different enantiomeric or diastereomeric forms. Thus any given compound referred to herein is intended to represent any one of a racemate, one or more enantiomeric forms, one or more diastereomeric forms, and mixtures thereof. Likewise, stereoisomerism or geometric isomerism related to a double bond is also possible, therefore in some cases the molecule could exist as (E)-isomer or (Z)-isomer (trans- and cis-isomers). If the molecule contains several double bonds, each double bond will have its own stereoisomerism, that could be the same or different than the stereoisomerism of the other double bonds of the molecule. All the stereoisomers including enantiomers, diastereoisomers and geometric isomers of the compounds referred to herein, and mixtures thereof, are considered within the scope of the present invention.

The compounds of the invention may be in crystalline form either as free compounds or as solvates (e.g. hydrates, alcoholates, particularly methanolates) and it is intended that both forms are within the scope of the present invention. Solvate may include water or non-aqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water. Methods of solvation are generally known within the art.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e. the capacity to occur in different crystalline forms). These different crystalline forms are typically known as "polymorphs". It is to be understood that when named or depicted by structure, the disclosed compounds and solvates (e.g., hydrates) also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of the invention or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of the invention or of its pharmaceutically acceptable salt, stereoisomer or solvate.

The invention also provides "metabolites" of the compounds described in the present description. A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups.

The invention also provides "prodrugs" of the compounds described in the present description. The term "prodrug", as used herein, is intended to represent covalently bonded carriers, which are capable of releasing the compound of the invention as active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the invention), amides (e.g., trifluoroacetylamino, acetylamino, and the like), and the like.

In additional preferred embodiments, the preferences described above for the different groups and substituents in the formulae above are combined. The present invention is also directed to such combinations.

Pharmaceutical Composition of the Invention

In a second aspect, the invention relates to a pharmaceutical composition comprising the compound of formula (II):

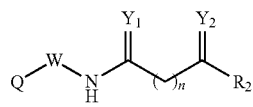

(II)

or a pharmaceutically acceptable salt, stereoisomer or solvate thereof,
wherein
$Y_1$=O, NH;
$Y_2$=O, NH;
W=O, NH
n=0, 1;
$R_2$=$OR_3$ or $NHR_4$, wherein $R_3$ is selected from H, $C_1$-$C_6$ alkyl, and aryl, and wherein $R_4$ is selected from H, OH, $C_1$-$C_6$ alkyl, aryl groups, —$NH_2$, —NH—$CH_3$ and —$NR_aR_b$, wherein $R_a$ and $R_b$ are independently selected $C_{1-6}$ alkyl groups or aryl groups,
Q is selected from a group consisting of:
a) 1-pyridine, 2-pyridine, 3-pyridine,
b) phenyl optionally substituted with one or more groups independently selected from $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, —NHOH, —NH—$NH_2$, —NH—$CH_3$ and —$NR_6R_7$, wherein $R_6$ and $R_7$ are independently selected from $C_{1-6}$ alkyl groups, aryl groups, —C(O)$R_5$, —OC(O)$R_5$, or —C(O)$OR_5$—, wherein $R_5$ is $C_{1-6}$ alkyl, aryl, or hydrogen.
c) 5-6 membered aromatic ring having one or more heteroatoms selected from N, S, and O and being optionally substituted with one or more groups independently selected from:
$C_{1-8}$ alkyl, linear or branched $C_{1-8}$ alkenyl, $C_{5-6}$ cycloalkyl,
phenyl as defined in b),
5-6 membered aromatic ring group having one or more heteroatoms selected from N, S, and O,
halogen,
($C_{1-6}$alkyl)$OCH_2$—,
$C_{1-6}$ alkoxy,
$NR_aR_b$, wherein $R_a$ and $R_b$ are independently selected from $C_{1-6}$ alkyl groups or aryl groups, and
NHC(O)$R_5$—, —C(O)NH—$R_5$, —OC(O)$R_5$, and —C(O)$OR_5$—, wherein $R_5$ is $C_{1-6}$ alkyl, aryl or hydrogen, and
d) a fused bicyclic ring containing at least one phenyl group and a $C_{5-6}$ aromatic heterocyclic group having one or more heteroatoms selected from N, S, and O, wherein the phenyl group of said fused bicyclic ring is optionally substituted with one or more groups independently selected from
$C_{1-8}$ alkyl, linear or branched $C_{1-8}$ alkenyl, $C_{5-6}$ cycloalkyl,
phenyl as defined in b),
5-6 membered aromatic ring group as defined in c),
halogen,
($C_{1-6}$alkyl)$OCH_2$—,
$C_{1-6}$alkoxy,
OH, —SH or —$SR_5$ wherein $R_5$ is $C_{1-6}$ alkyl, aryl or hydrogen,
$NR_6R_7$, wherein $R_6$ and $R_7$ are independently selected from $C_{1-6}$ alkyl groups, aryl groups, C(O)$R_5$, —OC(O)$R_5$, or —C(O)$OR_5$, wherein $R_5$ is $C_{1-6}$ alkyl, aryl or hydrogen, and
NHC(O)$R_5$—, —C(O)NH—$R_5$, —OC(O)$R_5$, or —C(O)$OR_5$—, wherein $R_5$ is $C_{1-6}$ alkyl, aryl, or hydrogen,
and a pharmaceutically acceptable excipient with the proviso that when $Y_1$=$Y_2$=O; n=0; $R_2$=—$NHNH_2$ and W is NH then Q is not a phenyl group.

In a preferred embodiment, the pharmaceutical composition of the invention comprises the compound of formula (II) wherein $Y_1$=O; $Y_2$=O; W=NH; n=0, 1; $R_2$=NHR$_4$, or aryl, and wherein $R_4$ is selected from OH, —NH$_2$, —NH—CH$_3$ and —NR$_a$R$_b$, wherein R$_a$ and R$_b$ are independently selected C$_{1-6}$ alkyl groups and Q is as previously described.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similar. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21$^{st}$ Edition, 2005; or "Handbook of Pharmaceutical Excipients", Rowe C. R.; Paul J. S.; Marian E. Q., sixth Edition Appropriate amounts of a compound of the invention as defined above, or a pharmaceutically acceptable salt, stereoisomer or solvate thereof can be formulated with pharmaceutically acceptable excipients and/or carriers to obtain a pharmaceutical composition for use in medicine, particularly in preventing and/or treating an infection caused by a bacterium, fungi or virus.

Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

In a preferred embodiment, the pharmaceutical composition of the invention comprises a compound according to the invention is a compound of formula (III)

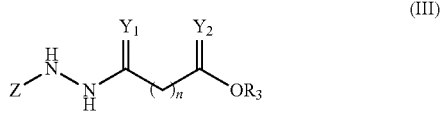

(III)

wherein
$Y_1$=O, NH;
$Y_2$=O, NH;
n=0, 1;
$R_3$ is selected from H and C$_1$-C$_6$ alkyl, and
Z=1-pyridine, 2-pyridine, 3-pyridine or phenyl optionally substituted with one or more groups independently selected from C$_{1-8}$ alkyl, C$_{2-8}$ alkenyl, halogen, —SH, —OR$_5$, —NO$_2$, C$_{1-6}$ alkoxy, C(O)NH—R$_5$, —C(O)OR$_5$, —OC(O)R$_5$, —CF$_3$, —CN, —NH$_2$, —NH—CH$_3$ and —NR$_6$R$_7$, wherein R$_5$ is C$_{1-6}$ alkyl, aryl or hydrogen and wherein R$_6$ and R$_7$ are independently selected from C$_{1-6}$ alkyl groups, aryl groups, —C(O)R$_5$, —NHC(O)R$_5$—, —C(O)NH—R$_5$, —OC(O)R$_5$, and —C(O)OR$_5$—.

In another preferred embodiment, the pharmaceutical composition of the invention comprises the compound according to the invention is a compound of formula (IV)

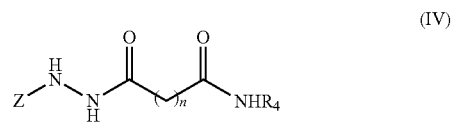

(IV)

wherein
n=0, 1;
$R_4$ is selected from H, OH, and NH$_2$,
Z=1-pyridine, 2-pyridine, 3-pyridine or phenyl, wherein the phenyl is optionally substituted with one or more groups independently selected from C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH—NH$_2$, —NH—CH$_3$ and —NR$_6$R$_7$, wherein R$_5$ is C$_{1-6}$ alkyl, aryl or hydrogen, wherein R$_6$ and R$_7$ are independently selected from C$_{1-6}$ alkyl groups, aryl groups, —C(O)R$_5$, —OC(O)R$_5$, or —C(O)OR$_5$, with the proviso that when $Y_1$=$Y_2$=O; n=0; R$_4$ is NH$_2$ then Z is not a phenyl group.

In a preferred embodiment, the pharmaceutical composition of the invention comprises a compound of formula (IV) wherein R$_4$ is NH$_2$.

In another preferred embodiment, the pharmaceutical composition of the invention comprises a compound of formula (V):

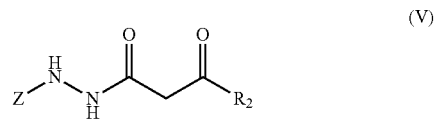

(V)

wherein
$R_2$=OR$_3$ or NHR$_4$, wherein R$_3$ is selected from H, C$_1$-C$_6$ alkyl and aryl, and wherein R$_4$ is selected from H, OH, C$_1$-C$_6$ alkyl, aryl groups, —NH$_2$, —NH—CH$_3$ and —NR$_a$R$_b$, wherein R$_a$ and R$_b$ are independently selected C$_{1-6}$ alkyl groups or aryl groups,
Z=1-pyridine, 2-pyridine, 3-pyridine or phenyl optionally substituted with one or more groups independently selected from C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH$_2$NH$_2$, —NH—CH$_3$ and —NR$_6$R$_7$, wherein R$_5$ is C$_{1-6}$ alkyl, aryl or hydrogen wherein R$_6$ and R$_7$ are independently selected from C$_{1-6}$ alkyl groups, aryl groups, —C(O)R$_5$, —OC(O)R$_5$, or —C(O)OR$_5$.

In a preferred embodiment, the pharmaceutical composition of the invention comprises a compound of formula (V) wherein R$_2$=NHR$_4$, wherein R$_4$ is selected from OH, —NH$_2$, —NH—CH$_3$ and —NR$_a$R$_b$, wherein R$_a$ and R$_b$ are independently selected C$_{1-6}$ alkyl groups and Z is as previously described.

In a more preferred embodiment, the pharmaceutical composition of the invention comprises a compound of formula (VI):

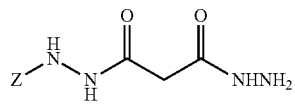
(VI)

wherein
Z=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, $NH_2$, NHOH, —$NH_2NH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

In another preferred embodiment, the pharmaceutical composition of the invention comprises a compound of formula (VII):

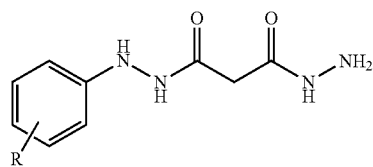
(VII)

wherein the phenyl group is optionally substituted with one or more groups independently selected from $C_{1-8}$ alkyl, $C_{2-8}$ alkenyl, halogen, —SH, —$OR_5$, —$SR_5$, OH, $NO_2$, C(O) NH—$R_5$, —C(O)$OR_5$, —OC(O)$R_5$, $CF_3$, CN, —$NH_2$, NHOH, —$NH_2NH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

In a preferred embodiment the pharmaceutical composition comprises a compound of formula (II) wherein $Y_1=Y_2=O$, n=0, and Q is a phenyl group optionally substituted in para position with a group selected from the group consisting of H, halogen, $CH_3$ and $OCH_3$.

In a preferred embodiment the pharmaceutical composition comprises a compound selected from the group consisting of:

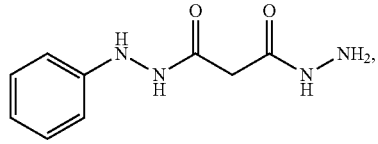
(Ia) MSG187

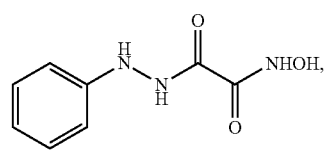
(Ib) MSG158

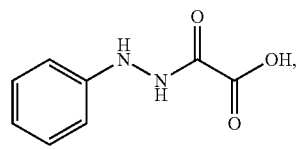
(Ic) MSG160

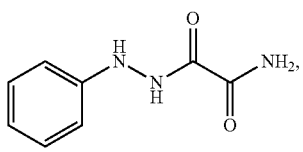
(Id) MSG159

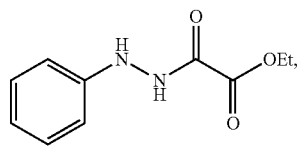
(Ie) MSG156

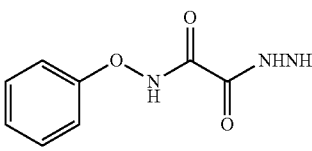
(If) MSG196

(Ig) MSG231

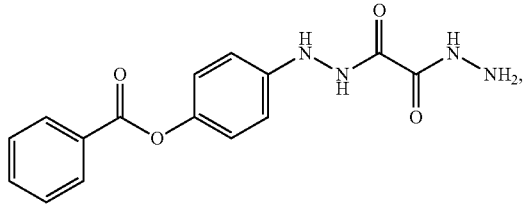

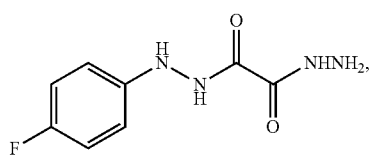
(IIb) MSG193

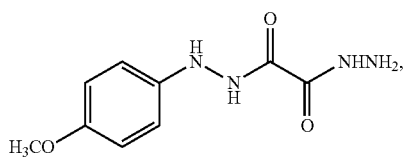
(IIc) MSG210

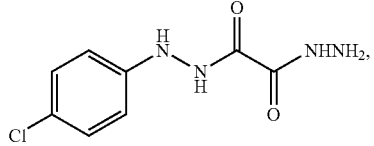
(IId) MSG214

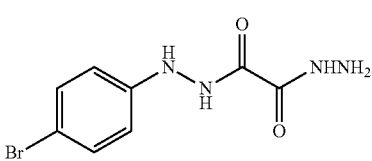
(IIe) MSG216

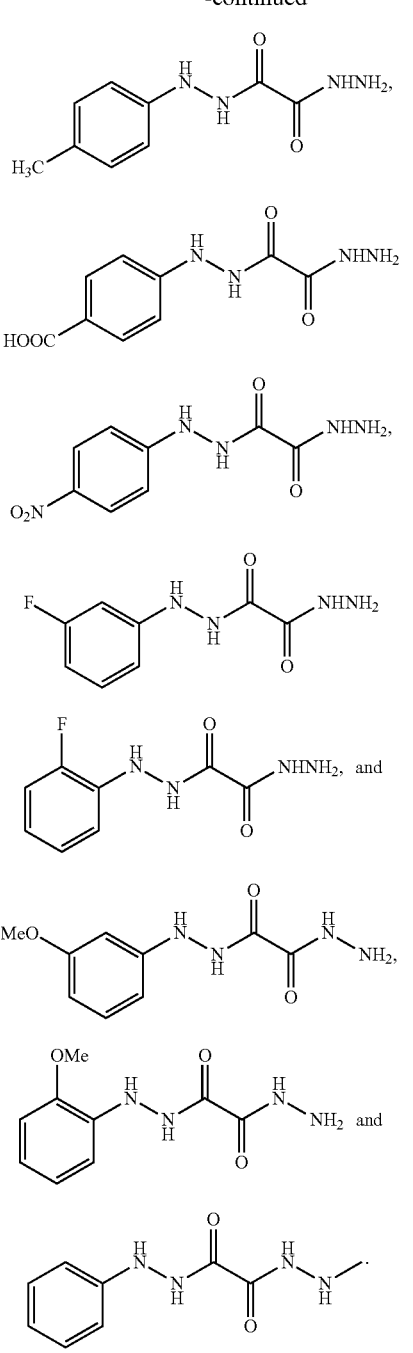

(IIf) MSG218
(IIg) MSG223
(IIh) MSG198
(IIi) MSG 227
(IIj) MSG235
(IIk) MSG 237
(IIl) MSG 239
(IIm) MSG161

In a more preferred embodiment, the pharmaceutical composition comprises a compound selected from the group consisting of (Ia) MSG187, (Ib) MSG158, (If) MSG196, (Ig) MSG231, (IIb) MSG193, (IIc) MSG210, (IId) MSG214, (IIe) MSG216, (IIf) MSG218, (IIg) MSG223, (IIh) MSG198, (IIi) MSG 227 and (IIj) MSG235.

The pharmaceutical compositions containing the compound of the invention as defined above, or a pharmaceutically acceptable salt, stereoisomer or solvate thereof according to the invention can occur at any pharmaceutical form of administration considered appropriate for the selected administration route, for example, by systemic (e.g. intravenous, subcutaneous, intramuscular injection), oral, parenteral or topical administration, for which it will include the pharmaceutically acceptable excipients necessary for formulation of the desired method of administration. Additionally, it is also possible to administer the composition comprising the compound of the invention as defined above, or a pharmaceutically acceptable salt, stereoisomer or solvate thereof of the invention intranasally or sublingually which allows systemic administration by a non-aggressive mode of administration. Also, intraventricular administration may be adequate. A preferred route of delivery is oral.

Those skilled in the art are familiar with the principles and procedures discussed in widely known.

Where necessary, the compound of the invention as defined above, or a pharmaceutically acceptable salt, stereoisomer or solvate thereof is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, compounds of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, the compounds of the invention as defined above, or a pharmaceutically acceptable salt, stereoisomer or solvate thereof may be administered in the form of transdermal patches or iontophoresis devices. In one embodiment, the compounds of the invention are administered as a transdermal patch, for example, in the form of sustained-release transdermal patch. Suitable transdermal patches are known in the art.

Several drug delivery systems are known and can be used to administer the agents or compositions of the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of a compound according to the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of the them.

Enteric coatings may be applied using conventional processes known to experts in the art, as described in, for example, Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

The present invention also encompasses the combination of the compounds of the invention or of its pharmaceutically acceptable salt, stereoisomer or solvate with other antimicrobial drugs. A combination of at least a compound of the invention and at least another antimicrobial drug may be formulated for its simultaneous, separate or sequential administration. This has the implication that the combination of the two compounds may be administered:

- as a combination that is being part of the same medicament formulation, the two compounds being then administered always simultaneously.
- as a combination of two units, each with one of the substances giving rise to the possibility of simultaneous, sequential or separate administration.

In a particular embodiment, the compound of the invention is independently administered from the other antimicrobial drug (i.e. in two units) but at the same time.

In another particular embodiment, the compound of the invention is administered first, and then the other antimicrobial drug is separately or sequentially administered.

In yet another particular embodiment, the other antimicrobial drug is administered first, and then the compound of the invention is administered, separately or sequentially, as defined.

"Antimicrobial drug", as used herein, relates to any drug capable of killing bacteria, viruses, fungi or parasites or inhibit their growth. Antimicrobial medicines can be grouped according to the microorganisms they act primarily against, antibacterial, antifungal, antiviral and antiparasitic. In a preferred embodiment, the antimicrobial drug is an antifungal drug.

In additional preferred embodiments, the preferences described above for the different groups and substituents in the formulae above are combined. The present invention is also directed to such combinations.

All the terms and embodiments previously described are equally applicable to this aspect of the invention.

Process for Obtaining the Compounds of the Invention

The invention also relates to a method for preparing the compound of formula (I) of the invention through the following reactions:

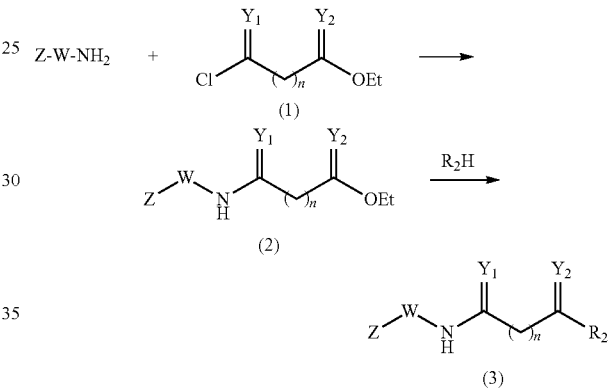

wherein
$Y_1$=O, NH;
$Y_2$=O, NH;
W=O, NH;
n=0, 1;
$R_2$=$OR_3$ or $NHR_4$, wherein $R_3$ is selected from the group consisting of H, $C_1$-$C_6$ alkyl, and aryl; and wherein $R_4$ is selected from the group consisting of H, OH, $C_1$-$C_6$ alkyl, aryl groups, —$NH_2$, —NH—$CH_3$ and —$NR_aR_b$, wherein $R_a$ and $R_b$ are independently selected $C_{1-6}$ alkyl groups or aryl groups;
Z=1-pyridine, 2-pyridine, 3-pyridine or phenyl, wherein the phenyl is optionally substituted with one or more groups independently selected from the group consisting of $C_{1-8}$ alkyl, $C_{2-3}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, —NHOH, —$NHNH_2$, —NH—$CH_3$ and —$NR_6R_7$, wherein $R_5$ is $C_{1-6}$ alkyl, aryl or hydrogen, wherein $R_6$ and $R_7$ are independently selected from $C_{1-6}$alkyl, aryl, —C(O)$R_5$, —OC(O)$R_5$, or —C(O)$OR_5$, with the proviso that when $Y_1$=$Y_2$=O; n=0; $R_2$=$NHNH_2$ and W is NH, then Z is not a group selected from the group consisting of a pyridine group, and a phenyl group wherein the phenyl group is optionally substituted with methyl, halogen, $NO_2$ or $OCH_3$ group.

Preferably, the reactions are carried out in the presence of an organic solvent, such as a cyclic or acyclic ether (e.g.

Et$_2$O, iPr$_2$O, tBu$_2$O, 1,4-dioxane, tetrahydrofuran, methyl-tetrahydrofuran), a hydrocarbonated solvent (e.g. pentane, hexane), a halogenated solvent (e.g. dichloromethane, chloroform), an alcohol (e.g. methanol, ethanol, propanol), an aromatic solvent (e.g. toluene, xylene), an amide (DMF, DMA) or mixtures thereof. In a particular embodiment, the reaction is performed in the presence of a halogenated solvent, such as dichloromethane.

In a more preferred embodiment the compound of formula (I) is prepared through reactions (1) and (2) in the presence of an organic solvent and the resulting compound is extracted in acid medium.

In a particular embodiment, the reaction is performed at a temperature between 0° C. and room temperature, in the presence of an organic solvent In a preferred embodiment, the method of the invention is for preparing a compound of formula (I) wherein Y$_1$=O; Y$_2$=O; W=NH; n=0, 1; R$_2$=NHR$_4$, wherein R$_4$ is selected from the group consisting of OH, —NH$_2$, —NH—CH$_3$ and —NRaRb, wherein Ra and Rb are independently selected C1-6 alkyl groups and Z is as previously described.

All the terms and embodiments previously described are equally applicable to this aspect of the invention.

Medical Uses

In a second aspect, the invention relates to a compound of formula (II):

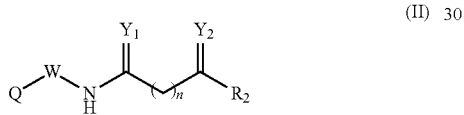

(II)

or a pharmaceutically acceptable salt, stereoisomer or solvate thereof,
wherein
Y$_1$=O, NH;
Y$_2$=O, NH;
W=O, NH;
n=0, 1;
R$_2$=OR$_3$ or NHR$_4$, wherein R$_3$ is selected from the group consisting of H, C$_1$-C$_6$ alkyl and aryl; and wherein R$_4$ is selected from the group consisting of H, OH, C$_1$-C$_6$ alkyl, aryl groups, —NH$_2$, —NH—CH$_3$ and —NR$_a$R$_b$, wherein R$_a$ and R$_b$ are independently selected C$_{1-6}$ alkyl groups or aryl groups;
Q is selected from a group consisting of:
a) 1-pyridine, 2-pyridine, 3-pyridine,
b) phenyl optionally substituted with one or more groups independently selected from the group consisting of C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, —NHOH, —NH—NH$_2$, —NH—CH$_3$ and —NR$_6$R$_7$, wherein R$_5$ is C$_{1-6}$ alkyl, aryl, or hydrogen, wherein R$_6$ and R$_7$ are independently selected from C$_{1-6}$ alkyl groups, aryl groups, —C(O)R$_5$—, —OC(O)R$_5$, or —C(O)OR$_5$,
c) 5-6 membered aromatic ring having one or more heteroatoms selected from the group consisting of N, S, and O and being optionally substituted with one or more groups independently selected from the group consisting of:

C$_{1-8}$ alkyl, linear or branched C$_{1-8}$ alkenyl, C$_{5-6}$ cycloalkyl,
phenyl as defined in b),
5-6 membered aromatic ring group having one or more heteroatoms selected from N, S, and O,
halogen,
(C$_{1-6}$alkyl)OCH$_2$—,
C$_{1-6}$alkoxy,
—NR$_a$R$_b$, wherein R$_a$ and R$_b$ are independently selected from C$_{1-6}$ alkyl groups or aryl groups, and
NHC(O)R$_5$—, —C(O)NH—R$_5$, —OC(O)R$_5$, and —C(O)OR$_5$—, wherein R$_5$ is C$_{1-6}$ alkyl, aryl or hydrogen, and
d) a fused bicyclic ring containing at least one phenyl group and a C$_{5-6}$ aromatic heterocyclic group having one or more heteroatoms selected from N, S, and O, wherein the phenyl group of said fused bicyclic ring is optionally substituted with one or more groups independently selected from
C$_{1-8}$ alkyl, linear or branched C$_{1-8}$ alkenyl, C$_{5-6}$ cycloalkyl,
phenyl as defined in b),
5-6 membered aromatic ring group as defined in c),
halogen,
(C$_{1-6}$alkyl)OCH$_2$—,
C$_{1-6}$alkoxy,
OH, —SH or —SR$_5$ wherein R$_5$ is C$_{1-6}$ alkyl, aryl or hydrogen,
NR$_6$R$_7$, wherein R$_6$ and R$_7$ are independently selected from C$_{1-6}$ alkyl groups, aryl groups, —C(O)R$_5$, —OC(O)R$_5$, or —C(O)OR$_5$, wherein R$_5$ is C$_{1-6}$ alkyl, aryl, or hydrogen, and
NHC(O)R$_5$—, —C(O)NH—R$_5$, —OC(O)R$_5$, and —C(O)OR$_5$—, wherein R$_5$ is C$_{1-6}$ alkyl, aryl or hydrogen,
with the proviso that when Y$_1$=O; Y$_2$=O; n=0; R$_2$=NHNH$_2$ and W is NH then Q is not a phenyl group, or a pharmaceutical composition comprising said compound and a pharmaceutically acceptable excipient for use in medicine.

In a preferred embodiment, the compound for use in medicine is the compound of formula (II) wherein Y$_1$=O; Y$_2$=O; W=NH; n=0, 1; R$_2$=NHR$_4$, wherein R$_4$ is selected from the group consisting of OH, —NH$_2$, —NH—CH$_3$ and —NR$_a$R$_b$, wherein R$_a$ and R$_b$ are independently selected C$_{1-6}$ alkyl groups; and Q is as previously described.

In a preferred embodiment, the compound for use in medicine according to the invention is a compound of formula (III)

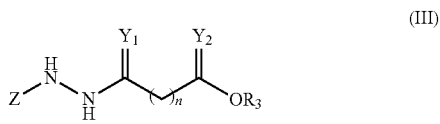

(III)

wherein
Y$_1$=O, NH;
Y$_2$=O, NH;
n=0, 1;
R$_3$ is selected from H and C$_1$-C$_6$ alkyl, and
Z=1-pyridine, 2-pyridine, 3-pyridine or phenyl optionally substituted with one or more groups independently selected from C$_{1-8}$ alkyl, C$_{2-8}$ alkenyl, halogen, —SH, —OR$_5$, —NO$_2$, C$_{1-6}$ alkoxy, C(O)NH—R$_5$, —C(O)OR$_5$, —OC(O)R$_5$, —CF$_3$, —CN, —NH$_2$, —NH—CH$_3$ and —NR$_6$R$_7$, wherein R$_5$ is C$_{1-6}$ alkyl, aryl or hydrogen and wherein R$_6$ and R$_7$ are independently selected from C$_{1-6}$ alkyl groups, aryl groups, —C(O)R$_5$, —NHC(O)R$_5$—, —C(O)NH—R$_5$, —OC(O)R$_5$, and —C(O)OR$_5$—.

In another preferred embodiment, the compound for use in medicine according to the invention is a compound of formula (IV)

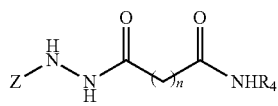

(IV)

wherein
n=0, 1;
R$_4$ is selected from H, OH, and NH$_2$,
Z=1-pyridine, 2-pyridine, 3-pyridine or phenyl, wherein the phenyl is optionally substituted with one or more groups independently selected from C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH—NH$_2$, —NH—CH and —NR$_6$R$_7$, wherein R$_5$ is C$_{1-6}$ alkyl, aryl or hydrogen, wherein R$_6$ and R$_7$ are independently selected from C$_{1-6}$ alkyl groups, aryl groups, —C(O)R$_5$, —OC(O)R$_5$, or —C(O)OR$_5$, with the proviso that when Y$_1$=Y$_2$=O; n=0 and R$_4$ is NH$_2$ then Z is not a phenyl group.

In a preferred embodiment, the compound for use in medicine is the compound of formula (IV) wherein R$_4$ is selected from OH and NH$_2$.

In another preferred embodiment, the compound for use in medicine according to the invention is a compound of formula (V):

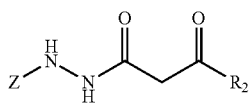

(V)

wherein
R$_2$=OR$_3$ or NHR$_4$, wherein R$_3$ is selected from H, C$_1$-C$_6$ alkyl and aryl, and wherein R$_4$ is selected from H, OH, C$_1$-C$_6$ alkyl, aryl groups, —NH$_2$, —NH—CH$_3$ and NR$_a$R$_b$, wherein R$_a$ and R$_b$ are independently selected C$_{1-6}$ alkyl groups or aryl groups,
Z=1-pyridine, 2-pyridine, 3-pyridine or phenyl optionally substituted with one or more groups independently selected from C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH$_2$NH$_2$, —NH—CH$_3$ and —NR$_6$R$_7$, wherein R$_5$ is C$_{1-6}$ alkyl, aryl or hydrogen wherein R$_6$ and R$_7$ are independently selected from C$_{1-6}$ alkyl groups, aryl groups, —C(O)R$_5$, —OC(O)R$_5$, or —C(O)OR$_5$.

In a preferred embodiment, the compound for use in medicine is a compound of formula (V) wherein R$_2$=NHR$_4$, wherein R$_4$ is selected from OH, —NH$_2$, —NH—CH$_3$ and —NR$_a$R$_b$, wherein R$_a$ and R$_b$ are independently selected C$_{1-6}$ alkyl groups.

In a more preferred embodiment, the compound for use in medicine according to the invention is a compound of formula (VI):

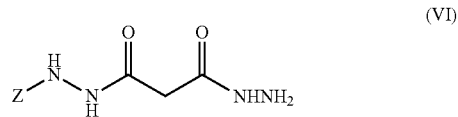

(VI)

wherein
Z=1-pyridine, 2-pyridine, 3-pyridine or phenyl, wherein the phenyl is optionally substituted with one or more groups independently selected from the group consisting of C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH$_2$NH$_2$, —NH—CH$_3$ and —NR$_6$R$_7$, wherein R$_5$ is C$_{1-6}$ alkyl, aryl or hydrogen wherein R$_6$ and R$_7$ are independently selected from C$_{1-6}$ alkyl groups, aryl groups, —C(O)R$_5$, —OC(O)R$_5$, or —C(O)OR$_5$.

In another preferred embodiment, the compound for use in medicine according to the invention is a compound of formula (VII):

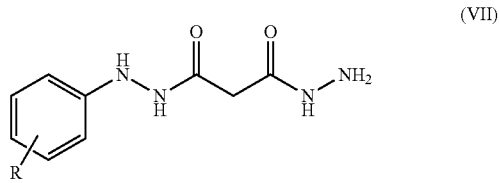

(VII)

wherein the phenyl group is optionally substituted with one or more groups independently selected from C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH$_2$NH$_2$, —NH—CH$_3$ and —NR$_6$R$_7$, wherein R$_5$ is C$_{1-6}$ alkyl, aryl or hydrogen wherein R$_6$ and R$_7$ are independently selected from C$_{1-6}$ alkyl groups, aryl groups, —C(O)R$_5$, —OC(O)R$_5$, or —C(O)OR$_5$.

In a more preferred embodiment, the compound of the invention for use in medicine is selected from the group consisting of:

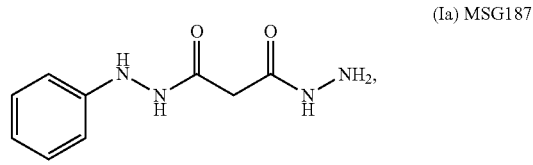

(Ia) MSG187

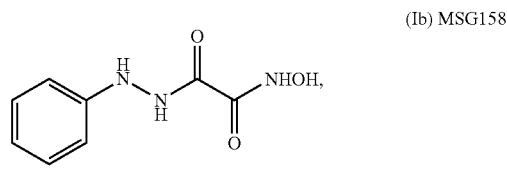

(Ib) MSG158

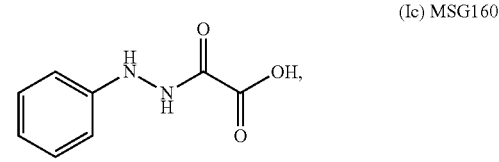 [SMILES: O=C(O)C(=O)NNc1ccccc1]

(Ic) MSG160

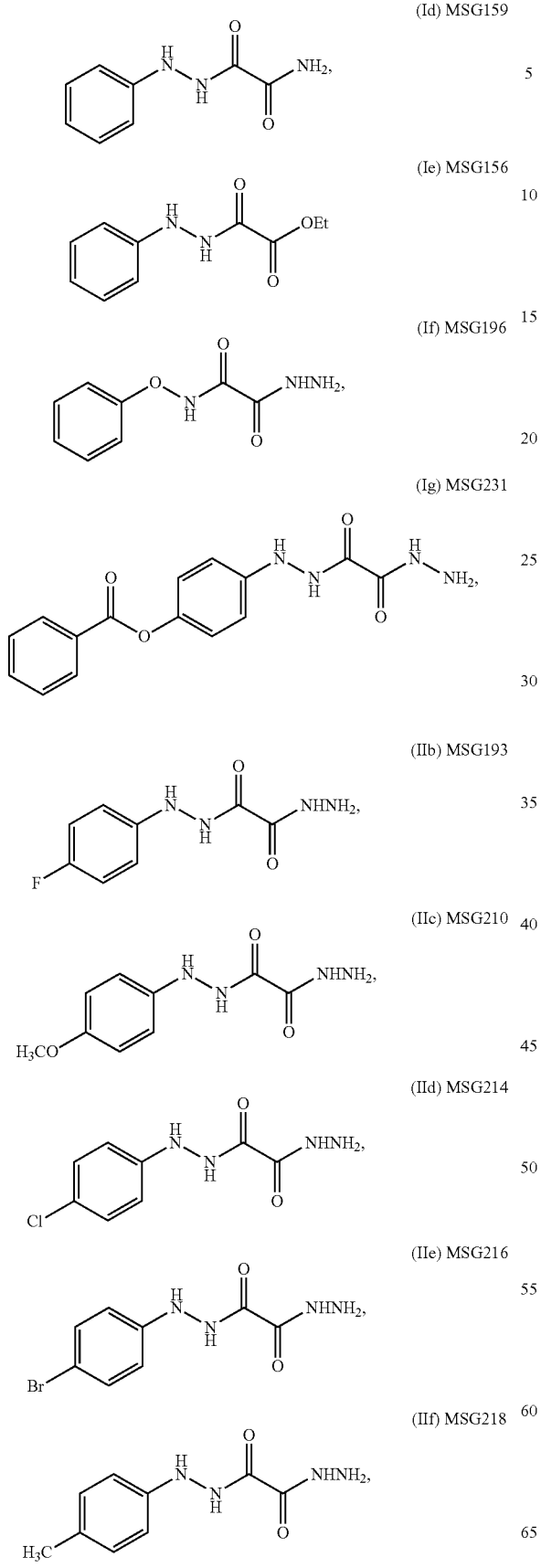

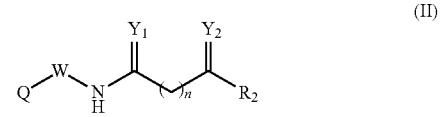

In an even more preferred embodiment, the compound of the invention for use in medicine is selected from the group consisting of (Ia) MSG187, (Ib) MSG158, (Ig) MSG231, (IIb) MSG193, (IIc) MSG210, (IId) MSG214, (IIe) MSG216, (IIf) MSG218, (IIg) MSG223, (IIh) MSG198, (IIi) MSG 227 and (IIj) MSG235.

In a third aspect, the invention relates to a pharmaceutical composition comprising a compound of formula (II)

$$\underset{H}{Q\diagdown W\diagdown N}\diagdown\overset{Y_1}{\underset{}{C}}\diagdown(C)_n\diagdown\overset{Y_2}{\underset{}{C}}\diagdown R_2 \qquad (II)$$

or a pharmaceutically acceptable salt, stereoisomer or solvate thereof, wherein
$Y_1$=O, NH;
$Y_2$=O, NH;
W=O, NH
n=0, 1;
$R_2$=$OR_3$ or $NHR_4$, wherein $R_3$ is selected from H, $C_1$-$C_6$ alkyl, and aryl, and wherein $R_4$ is selected from H, OH, $C_1$-$C_6$ alkyl, aryl groups, —$NH_2$, —NH—$CH_4$ and —$NR_aR_b$, wherein $R_a$ and $R_b$ are independently selected $C_{1-6}$ alkyl groups or aryl groups,
Q is selected from a group consisting of:
a) 1-pyridine, 2-pyridine, 3-pyridine,
b) phenyl optionally substituted with one or more groups independently selected from $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, $NH_2$, —NHOH, —NH—$NH_2$, —NH—$CH_3$ and —$NR_6R_7$, wherein $R_6$ and $R_7$ are independently selected $C_{1-6}$ alkyl groups, aryl groups, —C(O)$R_5$, —OC(O)$R_5$, or —C(O)$OR_5$—, wherein $R_5$ is $C_{1-6}$ alkyl, aryl, or hydrogen.

c) 5-6 membered aromatic ring having one or more heteroatoms selected from N, S, and O and being optionally substituted with one or more groups independently selected from:
$C_{1-8}$ alkyl, linear or branched $C_{1-8}$ alkenyl, $C_{5-6}$ cycloalkyl,
phenyl as defined in b),
5-6 membered aromatic ring group having one or more heteroatoms selected from N, S, and O,
halogen,
$(C_{1-6}alkyl)OCH_2$—,
$C_{1-6}$ alkoxy,
$NR_aR_b$, wherein $R_a$ and $R_b$ are independently selected from $C_{1-6}$ alkyl groups or aryl groups, and
$NHC(O)R_5$—, —$C(O)NH$—$R_5$, —$OC(O)R_5$, and —$C(O)OR_5$—, wherein $R_5$ is $C_{1-6}$ alkyl, aryl or hydrogen, and d) a fused bicyclic ring containing at least one phenyl group and a $C_{5-6}$ aromatic heterocyclic group having one or more heteroatoms selected from N, S, and O, wherein the phenyl group of said fused bicyclic ring is optionally substituted with one or more groups independently selected from
$C_{1-8}$ alkyl, linear or branched $C_{1-8}$ alkenyl, $C_{5-6}$ cycloalkyl,
phenyl as defined in b),
5-6 membered aromatic ring group as defined in c),
halogen,
$(C_{1-6}alkyl)OCH_2$—,
$C_{1-6}$ alkoxy,
OH, —SH or —$SR_5$ wherein $R_5$ is $C_{1-6}$ alkyl, aryl or hydrogen,
$NR_6R_7$, wherein $R_6$ and $R_7$ are independently selected from $C_{1-6}$ alkyl groups, aryl groups, $C(O)R_5$, —$OC(O)R_5$, or —$C(O)OR_5$, wherein $R_5$ is $C_{1-6}$ alkyl, aryl or hydrogen, and
$NHC(O)R_5$—, —$C(O)NH$—$R_5$, —$OC(O)R_5$, or —$C(O)OR_5$—, wherein $R_5$ is $C_{1-6}$ alkyl, aryl, or hydrogen,
and a pharmaceutically acceptable excipient for use in the prevention and/or treatment of an infection caused by a bacterium, fungus or virus.

In a preferred embodiment, the pharmaceutical composition comprising a compound of formula (II) is for use in the prevention and/or treatment of an infection caused by a fungus.

In another preferred embodiment, the pharmaceutical composition comprising a compound of formula (II), wherein $Y_1$=O, $Y_2$=O; W=NH, n=0, 1; $R_2$=$NHR_4$, wherein $R_4$ is selected from OH, —$NH_2$, —NH—$CH_3$ and —$NR_aR_b$, wherein $R_a$ and $R_b$ are independently selected $C_{1-6}$ alkyl group is for use in the prevention and/or treatment of an infection caused by a bacterium, fungus or virus. In another preferred embodiment, the pharmaceutical composition comprising a compound of formula (II), wherein $Y_1$=O, $Y_2$=O, W=NH, n=0, 1; $R_2$=$NHR_4$, wherein $R_4$ is selected from OH, —$NH_2$, —NH—$CH_3$ and —$NR_aR_b$, wherein $R_a$ and $R_b$ are independently selected $C_{1-6}$ alkyl group is for use in the prevention and/or treatment of an infection caused by a fungus.

Alternatively, the invention relates to a method for preventing and/or treating an infection caused by a bacterium, fungus or virus comprising administering a pharmaceutical composition comprising a compound of formula (II)

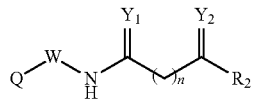

(II)

or a pharmaceutically acceptable salt, stereoisomer or solvate thereof,
wherein
$Y_1$=O, NH;
$Y_2$=O, NH;
W=O, NH
n=0, 1;
$R_2$=$OR_3$ or $NHR_4$, wherein $R_3$ is selected from H, $C_1$-$C_6$ alkyl, and aryl, and wherein $R_4$ is selected from H, OH, $C_1$-$C_6$ alkyl, aryl groups, —$NH_2$, —NH—$CH_3$ and —$NR_aR_b$, wherein $R_a$ and $R_b$ are independently selected $C_{1-6}$ alkyl groups or aryl groups,
Q is selected from a group consisting of
a) 1-pyridine, 2-pyridine, 3-pyridine,
b) phenyl optionally substituted with one or more groups independently selected from $C_{1-8}$ alkyl, $C_{2-8}$ alkenyl, halogen, —SH, —$OR_5$, —$SR_5$, OH, $NO_2$, $C(O)NH$—$R_5$, —$C(O)OR_5$, —$OC(O)R_5$, $CF_3$, CN, $NH_2$, —NHOH, —NH—$NH_2$, —NH—$CH_3$ and —$NR_6R_7$, wherein $R_6$ and $R_7$ are independently selected $C_{1-6}$ alkyl groups, aryl groups, —$C(O)R_5$, —$OC(O)R_5$, or —$C(O)OR_5$—, wherein $R_5$ is $C_{1-6}$ alkyl, aryl, or hydrogen,
c) 5-6 membered aromatic ring having one or more heteroatoms selected from N, S, and O and being optionally substituted with one or more groups independently selected from:
$C_{1-8}$ alkyl, linear or branched $C_{1-8}$ alkenyl, $C_{5-6}$ cycloalkyl,
phenyl as defined in b),
5-6 membered aromatic ring group having one or more heteroatoms selected from N, S, and O,
halogen,
$(C_{1-6}alkyl)OCH_2$—,
$C_{1-6}$ alkoxy,
$NR_aR_b$, wherein $R_a$ and $R_b$ are independently selected from $C_{1-6}$ alkyl groups or aryl groups, and
$NHC(O)R_5$—, —$C(O)NH$—$R_5$, —$OC(O)R_5$, and —$C(O)OR_5$—, wherein $R_5$ is $C_{1-6}$ alkyl, aryl or hydrogen, and
d) a fused bicyclic ring containing at least one phenyl group and a $C_{5-6}$ aromatic heterocyclic group having one or more heteroatoms selected from N, S, and O, wherein the phenyl group of said fused bicyclic ring is optionally substituted with one or more groups independently selected from
$C_{1-8}$ alkyl, linear or branched $C_{1-8}$ alkenyl, $C_{5-6}$ cycloalkyl,
phenyl as defined in b),
5-6 membered aromatic ring group as defined in c),
halogen,
$(C_{1-6}alkyl)OCH_2$—,
$C_{1-6}$ alkoxy,
OH, —SH or —$SR_5$ wherein $R_5$ is $C_{1-6}$ alkyl, aryl or hydrogen,
$NR_6R_7$, wherein $R_6$ and $R_7$ are independently selected from $C_{1-6}$ alkyl groups, aryl groups, $C(O)R_5$, —$OC(O)R_5$, or —$C(O)OR_5$, wherein $R_5$ is $C_{1-6}$ alkyl, aryl or hydrogen, and NHC(O)R$_5$—, —C(O)NH—R$_5$, —OC(O)R$_5$, or —C(O)OR$_5$—, wherein R$_5$ is C$_{1-6}$ alkyl, aryl, or hydrogen, to a subject in need thereof.

In a preferred embodiment, the method of the invention is for preventing and/or treating an infection caused by a fungus.

In another preferred embodiment the method of the invention comprises administering a pharmaceutical composition comprising a compound of formula (II) wherein Y$_1$=O; Y$_2$=O; W=NH; n=0, 1; R$_2$=NHR$_4$, wherein R$_4$ is selected from OH, —NH$_2$, —NH—CH$_3$ and —NR$_a$R$_b$, wherein R$_a$ and R$_b$ are independently selected C$_{1-6}$ alkyl group. In another preferred embodiment, the method for preventing and/or treating an infection caused by a fungus, comprises administering a pharmaceutical composition comprising a compound of formula (II) wherein Y$_1$=O, Y$_2$=O, W=NH, n=0, 1; R$_2$=NHR$_4$, wherein R$_4$ is selected from O, —NH$_2$, —NH—CH$_3$ and —NR$_a$R$_b$, wherein R$_a$ and R$_b$ are independently selected C$_{1-6}$ alkyl group.

Alternatively, the invention relates to a pharmaceutical composition comprising a compound of formula (II):

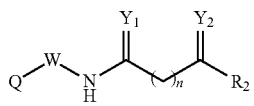

(II)

or a pharmaceutically acceptable salt, stereoisomer or solvate thereof,
wherein
Y$_1$=O, NH;
Y$_2$=O, NH;
W=O, NH
n=0, 1;
R$_2$=OR$_3$ or NH$_4$, wherein R$_3$ is selected from H, C$_1$-C$_6$ alkyl, and aryl, and wherein R$_4$ is selected from H, OH, C$_1$-C$_6$ alkyl, aryl groups, —NH$_2$, —NH—CH$_3$ and —NR$_a$R$_b$, wherein R$_a$ and R$_b$ are independently selected C$_{1-6}$ alkyl groups or aryl groups,
Q is selected from a group consisting of:
a) 1-pyridine, 2-pyridine, 3-pyridine,
b) phenyl optionally substituted with one or more groups independently selected from C$_{1-8}$ alkyl, C$_{2-8}$ alkenyl, halogen, —SH, —OR$_5$, —SR$_5$, O, NO$_2$, C(O)NH—R$_5$, —C(O)OR$_5$, —OC(O)R$_5$, CF$_3$, CN, NH$_2$, —NHOH, —NH—NH$_2$, —NH—CH$_3$ and —NR$_6$R$_7$, wherein R$_6$ and R$_7$ are independently selected C$_{1-6}$ alkyl groups, aryl groups, —C(O)R$_5$, —OC(O)R$_5$, or —C(O)OR$_5$—, wherein R$_5$ is C$_{1-6}$ alkyl, aryl, or hydrogen.
c) 5-6 membered aromatic ring having one or more heteroatoms selected from N, S, and O and being optionally substituted with one or more groups independently selected from:
C$_{1-8}$ alkyl, linear or branched C$_{1-8}$ alkenyl, C$_{5-6}$ cycloalkyl,
phenyl as defined in b),
5-6 membered aromatic ring group having one or more heteroatoms selected from N, S, and O,
halogen,
(C$_{1-6}$alkyl)OCH$_2$—,
C$_{1-6}$ alkoxy,
NR$_a$R$_b$, wherein R$_a$ and R$_b$ are independently selected from C$_{1-6}$ alkyl groups or aryl groups, and NHC(O)R$_5$—, —C(O)NH—R$_5$, —OC(O)R$_5$, and —C(O)OR$_5$—, wherein R$_5$ is C$_{1-6}$ alkyl, aryl or hydrogen, and d) a fused bicyclic ring containing at least one phenyl group and a C$_{5-6}$ aromatic heterocyclic group having one or more heteroatoms selected from N, S, and O, wherein the phenyl group of said fused bicyclic ring is optionally substituted with one or more groups independently selected from
C$_{1-8}$ alkyl, linear or branched C$_{1-8}$ alkenyl, C$_{5-6}$ cycloalkyl,
phenyl as defined in b),
5-6 membered aromatic ring group as defined in c),
halogen,
(C$_{1-6}$alkyl)OCH$_2$—,
C$_{1-6}$ alkoxy,
OH, —SH or —SR$_5$ wherein R$_5$ is C$_{1-6}$ alkyl, aryl or hydrogen,
NR$_6$R$_7$, wherein R$_6$ and R$_7$ are independently selected from C$_{1-6}$ alkyl groups, aryl groups, C(O)R$_5$, —OC(O)R$_5$, or —C(O)OR$_5$, wherein R$_5$ is C$_{1-6}$ alkyl, aryl or hydrogen, and
NHC(O)R$_5$—, —C(O)NH—R$_5$, —OC(O)R$_5$, or —C(O)OR$_5$—, wherein R$_5$ is C$_{1-6}$ alkyl, aryl, or hydrogen,
and a pharmaceutically acceptable excipient for the preparation of a medicament for preventing and/or treating an infection caused by a bacterium, fungus or virus.

In a preferred embodiment, the pharmaceutical composition comprising a compound of formula (II) is for the preparation of a medicament for preventing and/or treating an infection caused by a fungus.

In another preferred embodiment, the pharmaceutical composition for the preparation of a medicament for preventing and/or treating an infection caused by a bacterium, fungus or virus comprises a compound of formula (II) wherein Y$_1$=O; Y$_2$=O; W=NH; n=0, 1; R$_2$=NHR$_4$, wherein R$_4$ is selected from O, —NH$_2$, —NH—CH$_3$ and —NR$_a$R$_b$, wherein R$_a$ and R$_b$ are independently selected C$_{1-6}$ alkyl group. In another preferred embodiment, the pharmaceutical composition for preventing and/or treating an infection caused by a fungus comprises a compound of formula (II) wherein Y$_1$=O, Y$_2$=O, W=NH, n=0, 1; R$_2$=NHR$_4$, wherein R$_4$ is selected from OH, —NH$_2$, —NH—CH$_3$ and —NR$_a$R$_b$, wherein R$_a$ and R$_b$ are independently selected C$_{1-6}$ alkyl group. In a preferred embodiment Y$_1$=Y$_2$=O, n=0, and Q is a phenyl group optionally substituted in para position with a group selected from the group consisting of H, halogen, CH$_3$ and OCH$_3$.

In a preferred embodiment, the pharmaceutical composition for use in the prevention and/or treatment of an infection caused by a bacterium, fungus or virus comprises a compound of formula (III)

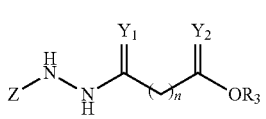

(III)

wherein
Y₁=O, NH;
Y₂=O, NH;
n=0, 1;
R₃ is selected from H and $C_1$-$C_6$ alkyl, and
Z=1-pyridine, 2-pyridine, 3-pyridine or phenyl optionally substituted with one or more groups independently selected from $C_{1-8}$ alkyl, $C_{2-8}$ alkenyl, halogen, —SH, —OR₅, —NO₂, $C_{1-6}$ alkoxy, C(O)NH—R₅, —C(O)OR₅, —OC(O)R₅, —CF₃, —CN, —NH₂, —NH—CH₃ and —NR₆R₇, wherein R₅ is $C_{1-6}$ alkyl, aryl or hydrogen and wherein R₆ and R₇ are independently selected from $C_{1-6}$ alkyl groups, aryl groups, —C(O)R₅, —NHC(O)R₅—, —C(O)NH—R₅, —OC(O)R₅, and —C(O)OR₅—.

In a preferred embodiment, the pharmaceutical composition comprising a compound of formula (III) is for use in the prevention and/or treatment of an infection caused by a fungus.

In another preferred embodiment, the pharmaceutical composition for use in the prevention and/or treatment of an infection caused by a bacterium, fungus or virus comprises a compound of formula (IV)

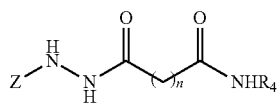

(IV)

wherein
n=0, 1;
R₄ is selected from H, OH, and NH₂,
Z=1-pyridine, 2-pyridine, 3-pyridine or phenyl, wherein the phenyl is optionally substituted with one or more groups independently selected from $C_{1-8}$ alkyl, $C_{2-8}$ alkenyl, halogen, —SH, —OR₅, —SR₅, OH, NO₂, C(O)NH—R₅, —C(O)OR₅, —OC(O)R₅, CF₃, CN, —NH₂, NHOH, —NH—NH₂, —NH—CH₃ and —NR₆R—, wherein R₅ is $C_{1-6}$ alkyl, aryl or hydrogen, wherein R₆ and R₇ are independently selected from $C_{1-6}$ alkyl groups, aryl groups, —C(O)R₅, —OC(O)R₅, or —C(O)OR₅.

In a preferred embodiment, the pharmaceutical composition comprising a compound of formula (IV) is for use in the prevention and/or treatment of an infection caused by a fungus.

In another preferred embodiment, the pharmaceutical composition for use in the prevention and/or treatment of an infection caused by a bacterium, fungus or virus comprises a compound of formula (IV) wherein R₄ is selected from OH, and NH₂. In another preferred embodiment, the pharmaceutical composition for use in the prevention and/or treatment of an infection caused by fungus comprises a compound of formula (IV) wherein R₄ is selected from OH, and NH₂.

In another preferred embodiment, the pharmaceutical composition for use in the prevention and/or treatment of an infection caused by a bacterium, fungus or virus comprises a compound of formula (V):

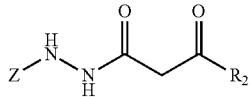

(V)

wherein
R₂=OR₃ or NHR₄, wherein R₃ is selected from H, $C_1$-$C_6$ alkyl and aryl, and wherein R₄ is selected from H, OH, $C_1$-$C_6$ alkyl, aryl groups, —NH₂, —NH—CH₃ and —NR$_a$R$_b$, wherein R$_a$ and R$_b$ are independently selected $C_{1-6}$ alkyl groups or aryl groups,
Z=1-pyridine, 2-pyridine, 3-pyridine or phenyl optionally substituted with one or more groups independently selected from $C_{1-8}$ alkyl, $C_{2-8}$ alkenyl, halogen, —SH, —OR₅, —SR₅, OH, NO₂, C(O)NH—R₅, —C(O)OR₅, —OC(O)R₅, CF₃, CN, —NH₂, NHOH, —NH₂NH₂, —NH—CH₃ and —NR₆R₇, wherein R₅ is $C_{1-6}$ alkyl, aryl or hydrogen wherein R₆ and R₇ are independently selected from $C_{1-6}$ alkyl groups, aryl groups, —C(O)R₅, —OC(O)R₅, or —C(O)OR₅.

In a preferred embodiment, the pharmaceutical composition comprising a compound of formula (V) is for use in the prevention and/or treatment of an infection caused by a fungus.

In a preferred embodiment, the pharmaceutical composition for use in the prevention of an infection caused by a bacterium, fungus or virus comprises a compound of formula (V) wherein R₂ is NHR₄, wherein R₄ is selected from OH, —NH₂ and —NH—CH₃. In another preferred embodiment, the pharmaceutical composition comprising a compound of formula (V) wherein R₂ is NHR₄, wherein R₄ is selected from OH, —NH₂ and —NH—CH₃ is for use in the prevention of an infection caused by a fungus.

In a more preferred embodiment, the pharmaceutical composition for use in the prevention and/or treatment of an infection caused by a bacterium, fungus or virus comprises a compound of formula (VI):

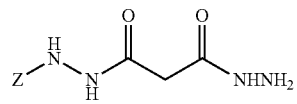

(VI)

wherein
Z=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, —SH, —OR₅, —SR₅, OH, NO₂, C(O)NH—R₅, —C(O)OR₅, —OC(O)R₅, CF₃, CN, —NH₂, NHOH, —NH₂NH₂, —NH—CH₃ and —NR₆R₇, wherein R₅ is $C_{1-6}$ alkyl, aryl or hydrogen wherein R₆ and R₇ are independently selected from $C_{1-6}$ alkyl groups, aryl groups, —C(O)R₅, —OC(O)R₅—, or —C(O)OR₅.

In a preferred embodiment, the pharmaceutical composition comprising a compound of formula (VI) is for use in the prevention and/or treatment of an infection caused by a fungus.

In another preferred embodiment, the pharmaceutical composition for use in the prevention and/or treatment of an infection caused by a bacterium, fungus or virus comprises a compound of formula (VII):

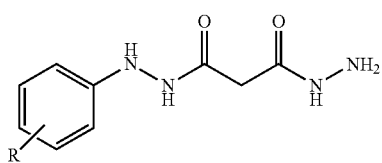

(VII)

wherein the phenyl group is optionally substituted with one or more groups independently selected from $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —$NH_2NH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

In a preferred embodiment, the pharmaceutical composition comprising a compound of formula (VII) is for use in the prevention and/or treatment of an infection caused by a fungus.

In another preferred embodiment of the medical uses, the compound is

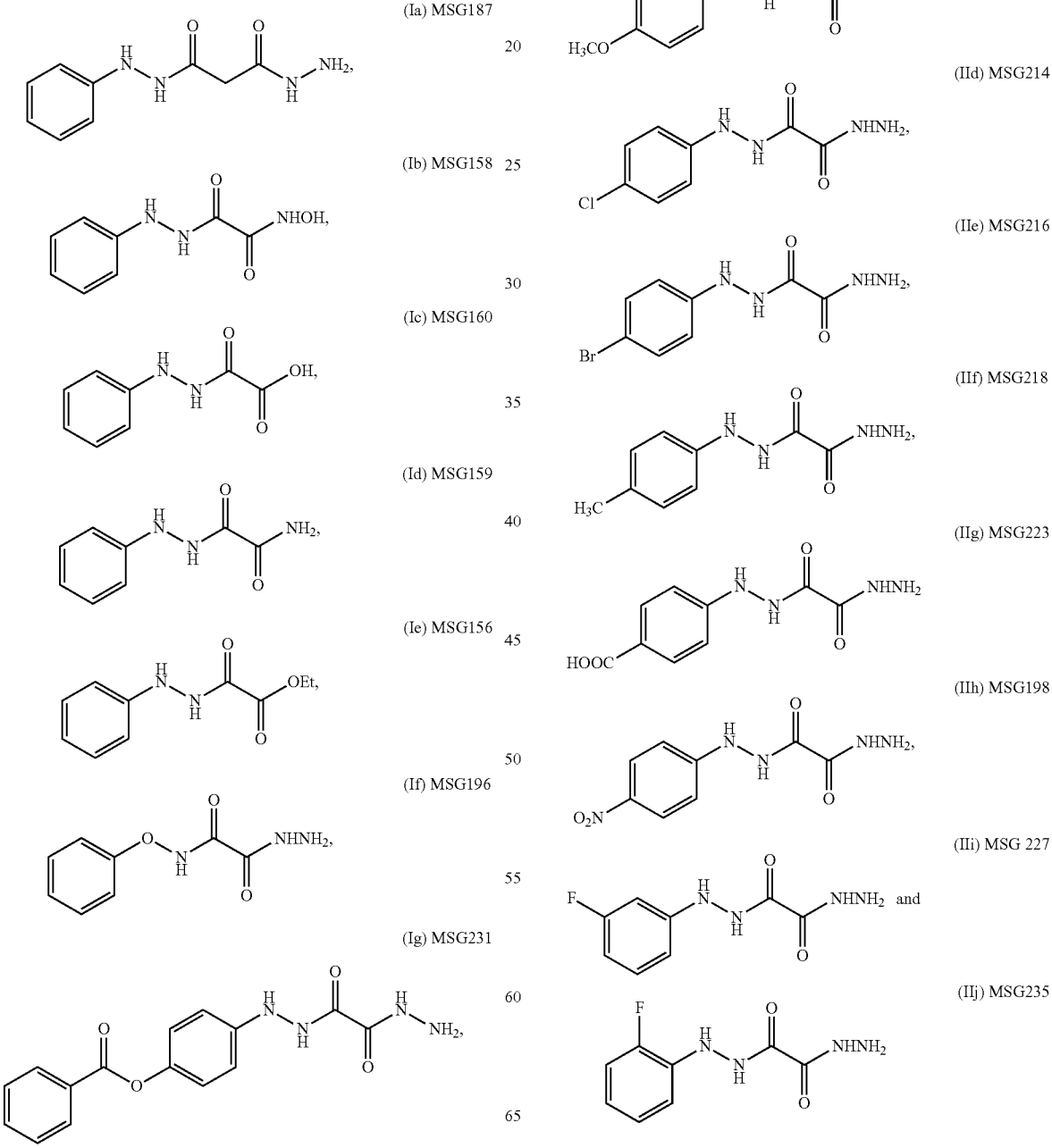

In a preferred embodiment of the medical uses of the invention, the pharmaceutical composition comprises a compound selected from the group consisting of (Ia) MSG187, (Ib) MSG158, (Ig) MSG231, (IIa) MSG119, (IIb) MSG193, (IIc) MSG210, (IId) MSG214, (IIe) MSG216, (IIf) MSG218, (IIg) MSG223, (IIh) MSG198 (IIi) MSG 227 and (IIj) MSG235.

In a more preferred embodiment, the pharmaceutical composition for use in the prevention and/or treatment of an infection caused by a bacterium comprises (If) MSG196
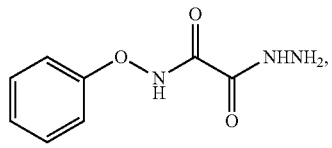

(IIc) MSG210
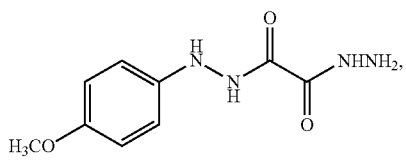

(IId) MSG214
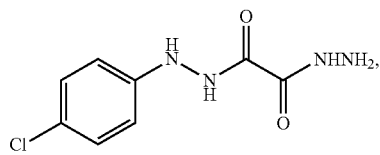

(IIe) MSG216
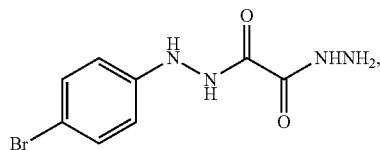

(IIf) MSG218
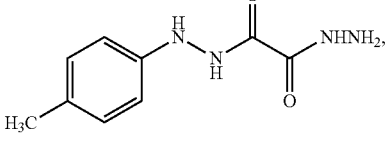

(IIa) MSG119
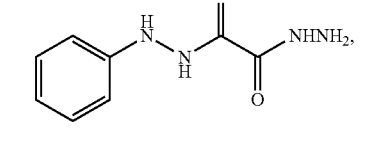

(Ig) MSG231
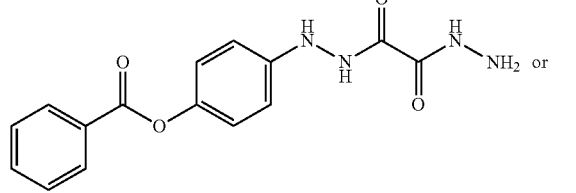

-continued (IIj) MSG235
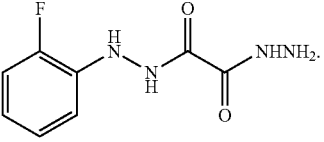

In another preferred embodiment, the pharmaceutical composition for use in the prevention and/or treatment of an infection caused by a fungi comprises (Ia) MSG187
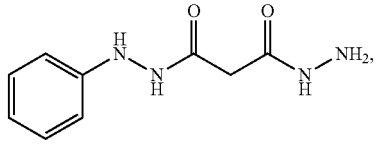

(IIb) MSG193
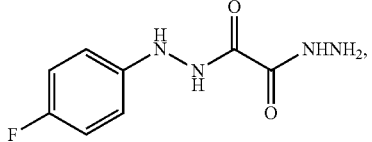

(IIa) MSG119
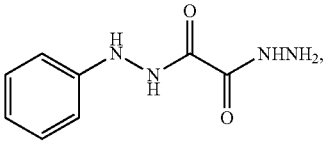

(IIc) MSG210
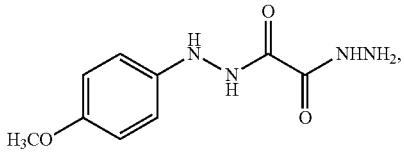

(IId) MSG214
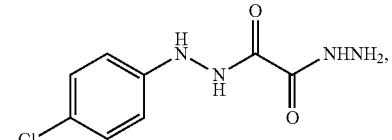

(IIe) MSG216
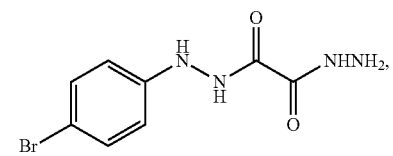

(IIf) MSG218
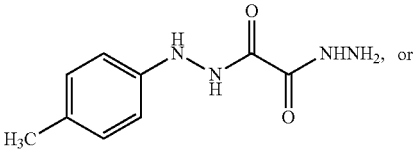

(IIi) MSG 227
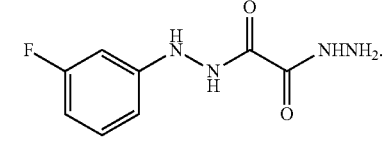

In a more preferred embodiment, the pharmaceutical composition for use in the prevention and/or treatment of an infection caused by a virus comprises

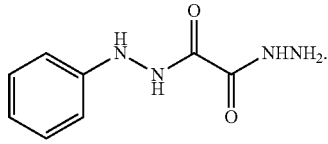

(IIa)MSG119

As used herein, the terms "treat", "treating" and "treatment" include in general the eradication, removal, reversion, alleviation, modification, or control of the infection after its onset.

As used herein, the terms "prevention", "preventing", "preventive", "prevent" and "prophylaxis" refer to the capacity of a given substance, composition or medicament to avoid, minimize or difficult the onset or development of an infection before its onset.

The term "subject" as used herein, relates to any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The term "infection", as used herein, relates to invasion by bacteria, viruses, fungi, protozoa or other microorganisms, referring to the undesired proliferation or presence of invasion of pathogenic microbes in a host organism. It includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

In a preferred embodiment, the infection is caused by a bacterium.

The term "bacterium" refers to both gram-negative and gram-positive bacterial cells capable of infecting and causing disease in a mammalian host, as well as producing infection-related symptoms in the infected host, such as fever or other signs of inflammation, intestinal symptoms, respiratory symptoms, dehydration, and the like.

In one embodiment the bacteria are gram-negative bacteria. In another embodiment the bacteria are gram-positive bacteria. In another further embodiment the bacteria are gram-positive bacteria together with gram-negative bacteria. In another embodiment there is only one bacteria specie or different bacteria species; one bacteria genus or different bacteria genus, infecting or causing disease.

In some embodiments, and without limitation, the bacteria is of a genus selected from the group consisting of *Acinetobacter, Actinobacillus, Aeromonas, Aggregatibacter, Agrobacterium, Bacillus, Bordetella, Brucella, Burkholderia, Campylobacter, Chromobacterium, Cyanobacteria, Enterobacter, Erwinia, Escherichia, Francisella, Fusobacterium, Haemophilus, Helicobacter, Klebsiella, Lactobacillus, Legionella, Listeria, Micrococcus, Moraxella, Mycobacterium, Neisseria, Nitrosonas, Nocardia, Obesumbacterium, Pantoea, Pasteurella, Pediococcus, Porphyronumas, Prevotella, Proteus, Pseudomonas, Ralstonia, Rhizobium, Rhodobacter, Salnnella, Serratia, Shigella, Staphylococcus, Streptococcus, Tannerella, Treponema, Tsukamurella, Vibrio, Xenorhabdus, Yersinia* and mixtures thereof. For example, in some embodiments and without limitation, the bacteria is of a species selected from the group consisting of *Aeromonas hydrophila, Aeromonas salmonicida, Acinetobacter baumannii, Aggregatibacter actinomvcetecomitans, Agrobacterium tumefaciens, Bacillus cereus, Bacillus subtilis, Burkholderia cepacia, Campylobacter jejuni, Chromobacterium violaceum, Enterobacter agglomeran, Erwinia carotovora, Erwinia chrysanthemi, Escherichia coli, Fusobacterium nucleatum, Haemophilus influenzae, Helicobacter pylori. Lactobacillus plantarum, Listeria monocytogenes, Klebsiella pneuoniae, Micrococcus luteus, Mycobacterium tuberculosis, Neisseria meningitidis, Neisseria gonorrhoeae, Nitrosomas europaea, Nocardia carnea, Obesumbacterium proteus, Pantoea stewartii, Pediococcus acidilactici, Prevotella intermedia, Porphyromonas gingivalis, Pseudononas aureofaciens, Pseudomonas aeruginosa, Pseudomonas phosphoreum, Pseudomonas syringae, Ralstonia solanacearum, Rhiszobium etli, Rhizobium leguminosarum, Rhodobacter sphaeroides, Salmonella typhimurium, Serratia liguefaciens, Serratia marcescens, Staphylococcus aureus, Staphylococcus epidermidis, Staphylococcus enteritis, Tannerella forsythensis, Treponema denticola, Tsukamurella pulmonis, Vibrio anguillarun, Vibrio fischeri, Vibrio cholerae, Vibrio harveyi, Vibrio parahaemolyticus, Vibrio alginolyticus, Vibrio vulnificus, Xenorhabdus nematophilus, Yersinia enterocolitica, Yersinia pestis, Yersinia pseudotuberculosis, Yersinia medievalis, Yersinia ruckeri* and mixtures thereof.

In a preferred embodiment of the medical use of a compound of the invention as defined above, or a pharmaceutically acceptable salt, stereoisomer or solvate thereof, the infection is caused by a Gram positive bacterium.

In another preferred embodiment, the Gram positive bacterium is from phylum Actinobacteria or from phylum Firmicutes and/or the Gram negative bacterium is from phylum proteobacteria.

In a more preferred embodiment, the bacterium from phylum Firmicutes is a bacterium from genus *Staphylococcus, Bacillus* or *Enterococcus*. In a more preferred embodiment, the bacterium from genus *Staphylococcus* is *S. aureus* or *S. epidermidis*, the bacterium from genus *Bacillus* is *B. cereus* and the bacterium from genus *Enterococcus* is *E. faecium* or *E. faecalis*.

In a more preferred embodiment, the bacterium from phylum Actinobacteria is a bacterium from genus *Nocardia, Tsukamurella* or *Mycobacterium*, the bacterium from phylum Firmicutes is a bacterium from genus *Streptococcus, Clostridium* or *Enterococcus* and/or the bacterium from phylum proteobacteria is from genus *Acinetobacter, Pseudomonas, Klebsiella, Escherichia* or *Enterobacter*.

In an even more preferred embodiment, the bacterium from the genus *Nocardia* is *N. carnea* or *N. cyriacigeorgica*, the bacterium from genus *Tsukamurella* is *T. pulmonis*, the bacterium from genus *Mycobacterium* is *M. abscessus*, the bacterium from genus *Streptococcus* is *S. pneumoniae, S. epidermidis* or *S. pyogenes*, the bacterium from genus *Klebsiella* is *K. pneunmoniae*, the bacterium from genus *Enterobacter* is *E. faecium, E. faecalis* or *E. cloacae*, the bacterium form genus *Escherichia* is *E. coli*, the bacterium from genus *Clostridium* is *C. difficile*, the bacterium from genus *Acinetobacter* is *A. baumannii* and/or the bacterium from genus *Pseudomonas* is *P. aeruginosa*.

In another preferred embodiment, the Gram negative bacterium is from phylum proteobacteria. In a more preferred embodiment, bacterium from phylum proteobacteria is from genus *Acinetobacter*, preferably *A. baumannii*, from genus *Pseudomonas*, preferably *P. aeruginosa* or from genus *Escherichia* preferably *E. coli*.

In another preferred embodiment of the medical use of a compound of formula (II) as defined above, or a pharmaceutically acceptable salt, stereoisomer or solvate thereof, the infection is caused by a fungus. In a more preferred embodiment, the fungus is selected from genus *Candida*, *Aspergillus*, *Saccharomyces* or *Scedosporium*. In an even more preferably embodiment, the fungus from genus *Candida* is *C. albicans, C. glabrata, C. tropicalis, C. lusitaniae, C guilliermondi* or *C. parapsilopsis*, the fungus from genus *Aspergillus* is *A. funigatus, A. flavus, A. niger* or *A. terreus* and the fungus from genus *Scedosporium* is *S. prolificans*.

In another preferred embodiment, the fungus is selected from genus *Candida*, *Aspergillus* or *Saccharomyces*.

In another preferred embodiment, the fungus from genus *Candida* is *C. albicans, C. parapsilopsis, C. tropicalis, C. lusitaniae, C. guilliermondi*, the fungus from genus *Aspergillus* is *A. fumigatus, A. flavus, A. niger* or *A. terreus* and/or the fungus from *Saccharomyces* is *S. cerevisiae*.

In another preferred embodiment of the medical use of a compound of the invention as defined above, or a pharmaceutically acceptable salt, stereoisomer or solvate thereof, the infection is caused by a virus.

The term "virus", refers to a small infectious agent that replicates only inside the living cells of other organism.

In some embodiments, and without limitation, the virus is selected from the group consisting of adenovirus, coxsackievirus, Epstein-Bar, Hepatitis A, B or C, herpes simplex type 1, herpes simplex type 2, cytomegalovirus, herpesvirus type 8, HIV, Influenza, Measles, mumps, human papillomavirus, parainfluenza, poliovirus, rabies, respiratory syncytial, rubella, varicella-zoster. In a preferred embodiment the virus is selected from HIV, herpes simplex 1, herpes simplex II, Suid herpesvirus 1 or Equine herpesvirus 1.

In a more preferred embodiment, the virus is HIV.

The present invention covers any combination of compounds and diseases.

For use in the prevention and/or treatment according to the invention, the compound of the invention or a pharmaceutically acceptable salt, solvate or isomer thereof or the pharmaceutical composition of the invention is present in an effective amount.

The term "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination.

Even though individual needs vary, determination of optimal ranges for effective amounts of the agent of the invention belongs to the common experience of those experts in the art. In general, the dosage needed to provide an effective amount of such compound, which can be adjusted by one expert in the art will vary depending on age, health, fitness, sex, diet, weight, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

The effective quantity of the compound of the invention can vary within a wide range and, in general, will vary depending on the particular circumstances of application, duration of the exposure and other considerations. In a particular embodiment, the dose ranges between 0.05 mg/kg and 50 mg/kg, more preferably between 1 mg/kg and 20 mg/kg.

In a preferred embodiment the effective amount is between about between about 0.005% and about 0.04% weight, between about 0.0075% weight and about 0.0375% weight, between about 0.001% weight and about 0.035% weight, between about 0.00125% weight and about 0.0325% weight, between about 0.0015% weight and about 0.0325% weight, between about 0.00175% weight and about 0.03% weight, and more preferably between about 0.0018% weight and about 0.032% weight. In a particular embodiment, the effective amount is between about 0.005% and about 0.02% weight, preferably between about 0.005% weight and about 0.015% weight, more preferably between about 0.005% weight and about 0.01% weight. In some embodiments the effective amount is about 0.001% weight, about 0.002% weight, about 0.003% weight or about 0.004% weight. The percentages (% w/w) are expressed as weight of the compound of the invention or a pharmaceutically acceptable salt, solvate or isomer thereof by the total weight of the composition comprising the compound or by weight of the foodstuff, foodstuff package, medical device or surface.

In another embodiment the effective amount is expressed in µg/mL or µg/g (µg of the compound of the invention or a pharmaceutically acceptable salt, solvate or isomer thereof by mL or g of the composition comprising the compound), therefore effective amount is about 75 and about 375 µg/ml (or µg/g), between about 100 and about 350 µg/mL (or µg/g), between about 125 and about 325 µg/mL (or µg/g), between about 150 and about 325 µg/mL (or g/g), between about 175 and about 300 µg/ml (or µg/g), and more preferably between about 180 and about 320 µg/ml (or µg/g). In a particular embodiment, the effective amount is between about 50 and about 200 µg/mL (or µg/g), preferably between 50 and about 150 µg/mL (or µg/g), more preferably between about 50 and about 100 µg/mL (or µg/g). In some embodiments the effective amount is about 100 µg/mL (or µg/g), about 200 µg/mL (or µg/g), about 300 µg/mL (or µg/g) or about 400 µg/mL (or g/g).

When the compound of the invention or a salt, solvate or isomer thereof as defined herein is present on a surface, it is preferably in an effective amount of between about 1 and about 200 µg/cm², preferably between about 1 and about 100 µg/cm², preferably between about 1 and about 50 µg/cm², more preferably between about 5 and about 300 µg/cm².

Additional aspects:

1. A compound of formula (I):

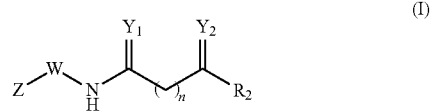

or a pharmaceutically acceptable salt, stereoisomer or solvate thereof,
wherein
$Y_1$=O, NH;
$Y_2$=O, NH;
W=O, NH;
n=0, 1;
$R_2$=$OR_3$ or $NHR_4$, wherein $R_3$ is selected from the group consisting of H, $C_1$-$C_6$ alkyl, and aryl; and wherein $R_4$ is selected from the group consisting of H, OH, $C_1$-$C_6$ alkyl, aryl groups, —$NH_2$, —NH—$CH_3$ and —$NR_aR_b$, wherein $R_a$ and $R_b$ are independently selected $C_{1-6}$ alkyl groups or aryl groups;
Z=1-pyridine, 2-pyridine, 3-pyridine or phenyl, wherein the phenyl is optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —NH—$NH_2$, —NH—$CH_3$ and —$NR_6R_7$, wherein $R_5$ is $C_{1-6}$ alkyl, aryl or hydrogen, wherein $R_6$ and $R_7$ are independently selected from $C_{1-6}$ alkyl, aryl, —C(O)$R_5$, —OC(O)$R_5$, or —C(O)$OR_5$, with the proviso that when $Y_1$=$Y_2$=O; n=0; $R_2$=$NHNH_2$ and W is NH then Z is not a group selected from the group consisting of a pyridine group, and a phenyl group wherein the phenyl group is optionally substituted with methyl, halogen, $NO_2$ or $OCH_3$ group.

2. The compound as defined in aspect 1, wherein $R_2$ is NH—$NH_2$ and/or wherein n is 1 and $Y_1$=$Y_2$=O.

3. The compound as defined in aspect 1 or 2, wherein Z is a phenyl group optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, NHOH, —$NHNH_2$, —NH—$CH_3$ and —$NR_6R_7$, wherein $R_5$ is $C_{1-6}$ alkyl, aryl or hydrogen wherein $R_6$ and $R_7$ are independently selected from $C_{1-6}$ alkyl groups, aryl groups, —C(O)$R_5$, —OC(O)$R_5$, or —C(O)$OR_5$.

4. The compound as defined in aspect 1, having the following formula:

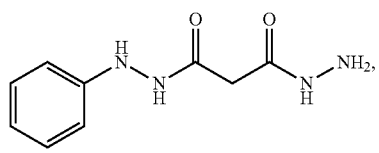
(Ia) MSG187

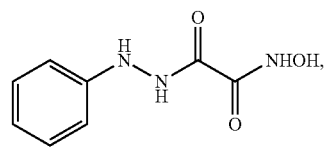
(Ib) MSG158

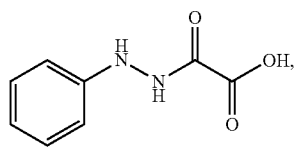
(Ic) MSG160

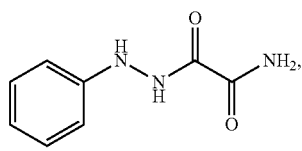
(Id) MSG159

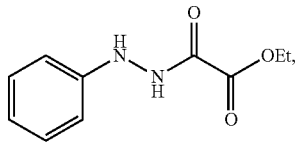
(Ie) MSG156

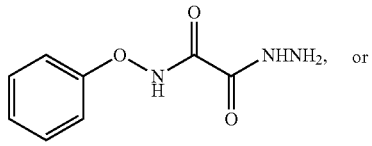
(If) MSG196

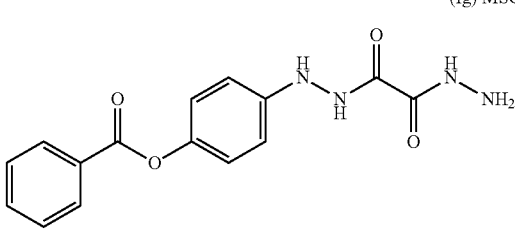
(Ig) MSG231

5. A compound of formula (II):

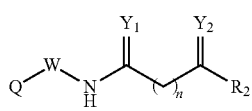
(II)

or a pharmaceutically acceptable salt, stereoisomer or solvate thereof,
wherein
$Y_1$=O, NH;
$Y_2$=O, NH;
W=O, NH;
n=0, 1;
$R_2$=$OR_3$ or $NHR_4$, wherein $R_3$ is selected from the group consisting of H, $C_1$-$C_6$ alkyl and aryl; and wherein $R_4$ is selected from the group consisting of H, OH, $C_1$-$C_6$ alkyl, aryl groups, —$NH_2$, —NH—$CH_3$ and —$NR_aR_b$, wherein $R_a$ and $R_b$ are independently selected $C_{1-6}$ alkyl groups or aryl groups;
Q is selected from a group consisting of:
a) 1-pyridine, 2-pyridine, 3-pyridine,
b) phenyl optionally substituted with one or more groups independently selected from the group consisting of $C_{1-8}$ alkyl, $C_{2-8}$ alkenyl, halogen, —SH, —$OR_5$, —$SR_5$, OH, $NO_2$, C(O)NH—$R_5$, —C(O)$OR_5$, —OC(O)$R_5$, $CF_3$, CN, —$NH_2$, —NHOH, —NH—$NH_2$, —NH—$CH_3$ and —$NR_6R_7$, wherein $R_5$ is $C_{1-6}$ alkyl, aryl, or hydrogen, wherein $R_6$ and $R_7$ are independently selected from $C_{1-6}$ alkyl groups, aryl groups, —C(O)$R_5$—, —OC(O)$R_5$, or —C(O)$OR_5$,
c) 5-6 membered aromatic ring having one or more heteroatoms selected from the group consisting of N, S, and O and being optionally substituted with one or more groups independently selected from the group consisting of:
$C_{1-8}$ alkyl, linear or branched $C_{1-8}$ alkenyl, $C_{5-6}$ cycloalkyl,
phenyl as defined in b),
5-6 membered aromatic ring group having one or more heteroatoms selected from N, S, and O, halogen,
(C$_{1-6}$alkyl)OCH$_2$—,
C$_{1-6}$ alkoxy,
—NR$_a$R$_b$, wherein R$_a$ and R$_b$ are independently selected from C$_{1-6}$ alkyl groups or aryl groups, and
NHC(O)R$_5$—, —C(O)NH—R$_5$, —OC(O)R$_5$, and —C(O)OR$_5$—, wherein R$_5$ is C$_{1-6}$ alkyl, aryl or hydrogen, and d) a fused bicyclic ring containing at least one phenyl group and a C$_{5-6}$ aromatic heterocyclic group having one or more heteroatoms selected from N, S, and O, wherein the phenyl group of said fused bicyclic ring is optionally substituted with one or more groups independently selected from
C$_{1-8}$ alkyl, linear or branched C$_{1-8}$ alkenyl, C$_{5-6}$ cycloalkyl,
phenyl as defined in b),
5-6 membered aromatic ring group as defined in c),
halogen,
(C$_{1-6}$alkyl)OCH$_2$—,
C$_{1-6}$alkoxy,
OH, —SH or —SR$_5$ wherein R$_5$ is C$_{1-6}$ alkyl, aryl or hydrogen,
—NR$_6$R$_7$, wherein R$_6$ and R$_7$ are independently selected from C$_{1-6}$ alkyl groups, aryl groups, —C(O)R$_5$, —OC(O)R$_5$, or —C(O)OR$_5$, wherein R$_5$ is C$_{1-6}$ alkyl, aryl, or hydrogen, and
NHC(O)R$_5$—, —C(O)NH—R$_5$, —OC(O)R$_5$, and —C(O)OR$_5$—, wherein R$_5$ is C$_{1-6}$ alkyl, aryl or hydrogen,
with the proviso that when Y$_1$=Y$_2$=O; n=0; R$_2$=NHNH$_2$ and W is NH then Q is not a phenyl group,
or a pharmaceutical composition comprising said compound and a pharmaceutically acceptable excipient for use in medicine.

6. A pharmaceutical composition comprising a compound of formula (II)

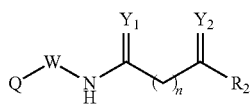

(II)

or a pharmaceutically acceptable salt, stereoisomer or solvate thereof,
wherein
Y$_1$=O, NH;
Y$_2$=O, NH;
W=O, NH
n=0, 1;
R$_2$=OR$_3$ or NHR$_4$, wherein R$_3$ is selected from H, C$_1$-C$_6$ alkyl, and aryl, and wherein R$_4$ is selected from H, OH, C$_1$-C$_6$ alkyl, aryl groups, —NH$_2$, —NH—CH$_3$ and NR$_a$R$_b$, wherein R$_a$ and R$_b$ are independently selected C$_{1-6}$ alkyl groups or aryl groups,
Q is selected from a group consisting of:
a) 1-pyridine, 2-pyridine, 3-pyridine,
b) phenyl optionally substituted with one or more groups independently selected from C$_{1-8}$ alkyl, C$_{2-8}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, NH$_2$, —NHOH, —NH—NH$_2$, —NH—CH$_3$ and —NR$_6$R$_7$, wherein R$_5$ is C$_{1-6}$ alkyl, aryl, or hydrogen, wherein R$_6$ and R$_7$ are independently selected C$_{1-6}$ alkyl groups, aryl groups, —C(O)R$_5$, —OC(O)R$_5$, or —C(O)OR$_5$—,
c) 5-6 membered aromatic ring having one or more heteroatoms selected from N, S, and O and being optionally substituted with one or more groups independently selected from:
C$_{1-8}$ alkyl, linear or branched C$_{1-8}$ alkenyl, C$_{5-6}$ cycloalkyl,
phenyl as defined in b),
5-6 membered aromatic ring group having one or more heteroatoms selected from N, S, and O,
halogen,
(C$_{1-6}$alkyl)OCH$_2$—,
C$_{1-6}$ alkoxy,
NR$_a$R$_b$, wherein R$_a$ and R$_b$ are independently selected from C$_{1-6}$ alkyl groups or aryl groups, and
NHC(O)R$_5$—, —C(O)NH—R$_5$, —OC(O)R$_5$, and —C(O)OR$_5$—, wherein R$_5$ is C$_{1-6}$ alkyl, aryl or hydrogen, and d) a fused bicyclic ring containing at least one phenyl group and a C$_{5-6}$ aromatic heterocyclic group having one or more heteroatoms selected from N, S, and O, wherein the phenyl group of said fused bicyclic ring is optionally substituted with one or more groups independently selected from
C$_{1-8}$ alkyl, linear or branched C$_{1-8}$ alkenyl, C$_{5-6}$ cycloalkyl,
phenyl as defined in b),
5-6 membered aromatic ring group as defined in c),
halogen,
(C$_{1-6}$alkyl)OCH$_2$—,
C$_{1-6}$ alkoxy,
OH, —SH or —SR$_5$ wherein R$_5$ is C$_{1-6}$ alkyl, aryl or hydrogen,
NR$_6$R$_7$, wherein R$_6$ and R$_7$ are independently selected from C$_{1-6}$ alkyl groups, aryl groups, C(O)R$_5$, —OC(O)R$_5$, or —C(O)OR$_5$, wherein R$_5$ is C$_{1-6}$ alkyl, aryl or hydrogen, and
NHC(O)R$_5$—, —C(O)NH—R$_5$, —OC(O)R$_5$, or —C(O)OR$_5$—, wherein R$_5$ is C$_{1-6}$ alkyl, aryl, or hydrogen,
and a pharmaceutically acceptable excipient for use in the prevention and/or treatment of an infection caused by a bacterium, fungus or virus.

7. A pharmaceutical composition for use according to any of aspects 5 or 6 wherein Y$_1$=Y$_2$=O, n=0, and Q is a phenyl group optionally substituted in para position with a group selected from the group consisting of H, halogen, CH$_3$ and OCH$_3$.

8. A pharmaceutical composition for use according to aspect 6 wherein the compound is selected from the group consisting of:

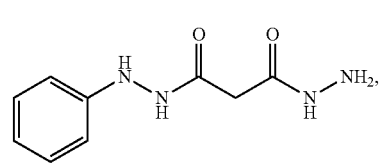

(Ia) MSG187

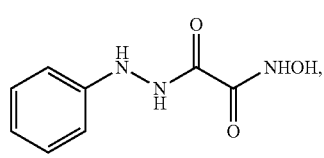

(Ib) MSG158

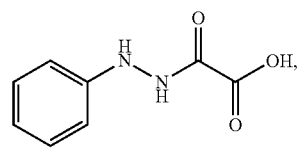

(Ic) MSG160

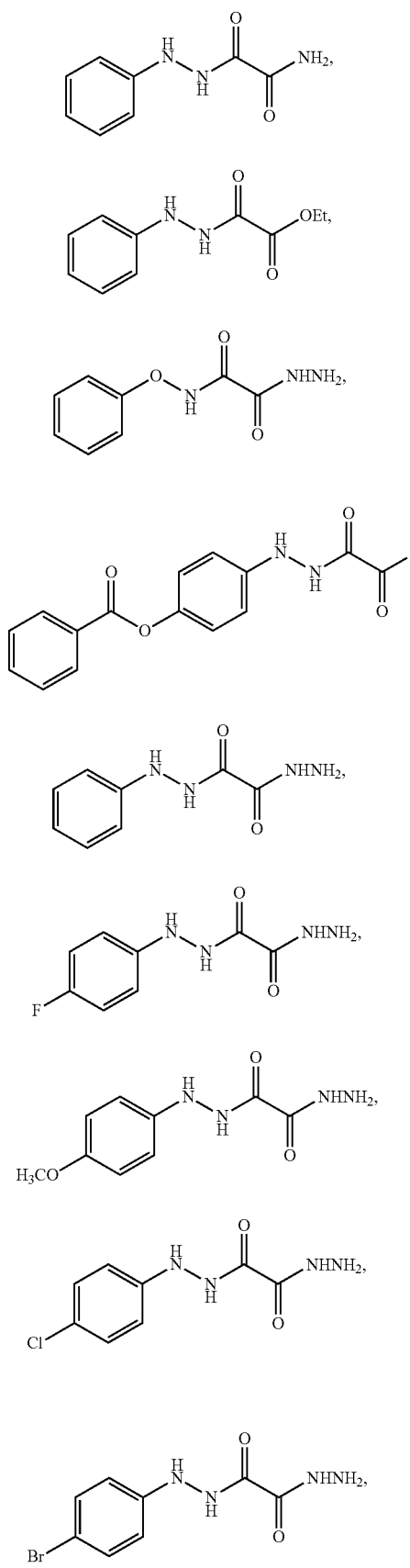
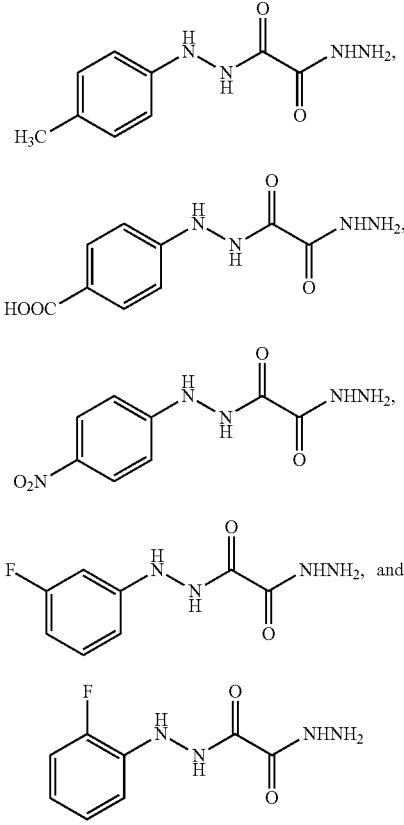

9. The pharmaceutical composition for use according to any of aspects 6 to 8 wherein the bacterium is a Gram positive bacterium or a Gram-negative bacterium.

10. The pharmaceutical composition for use according to aspect 9, wherein the Gram positive bacterium is from phylum Actinobacteria or from phylum Firmicutes and/or the Gram negative bacterium is from phylum proteobacteria.

11. The pharmaceutical composition for use according to aspect 10 wherein the bacterium from phylum Actinobacteria is a bacterium from genus *Nocardia, Tsukamurella* or *Mycobacterium*, the bacterium from phylum Firmicutes is a bacterium from genus *Streptococcus, Clostridium* or *Enterococcus* and/or the bacterium from phylum proteobacteria is from genus *Acinetobacter, Pseudomonas, Klebsiella, Escherichia* or *Enterobacter*.

12. The pharmaceutical composition for use according to aspect 11 wherein the bacterium from the genus *Nocardia* is *N. carnea* or *N. cyriacigeorgica*, the bacterium from genus *Tsukamurella* is *T. pulmonis*, the bacterium from genus *Mycobacterium* is *M. abscessus*, the bacterium from genus *Streptococcus* is *S. pneumoniae, S. epidermidis* or *S. pyogenes*, the bacterium from genus *Klebsiella* is *K. pneumoniae*, the bacterium from genus *Enterobacter* is *E. faecium, E. faecalis* or *E. cloacae*, the bacterium form genus *Escherichia* is *E. coli*, the bacterium from genus *Clostridium* is *C. difficile*, the bacterium from genus *Acinetobacter* is *A. baumannii* and/or the bacterium from genus *Pseudononas* is *P. aeruginosa*.

13. The pharmaceutical composition for use according to any of aspects 6 to 8 wherein the fungi is selected from genus *Candida, Aspergillus* or *Saccharomyces*.

14. The pharmaceutical composition for use according to aspect 13 wherein the fungus from genus *Candida* is *C. albicans*, *C. parapsilopsis*, *C. tropicalis*, *C. lusitaniae*, *C. guilliermondi*, the fungus from genus *Aspergillus* is *A. funigatus*, *A. flavus*, *A. niger* or *A. terreus* and/or the fungus from *Saccharomyces* is *S. cerevisiae*.

15. The pharmaceutical composition for use according to any of aspects 6 to 8 wherein the virus is HIV.

All the terms and embodiments previously described are equally applicable to this aspect of the invention.

The invention will be described by way of the following examples which are to be considered as merely illustrative and not limitative of the scope of the invention.

Materials and Methods

Synthesis Process of Some Compounds Belonging to the Invention

Step 1

The various phenylhydrazines (2.5 mmol, 2 eq) and ethyl chlorooxoacetate or malonate (1.25 mmol, 1 eq) were dissolved in $CH_2Cl_2$. The reaction mixture was stirred at 0° C. for 10-15 min. The reaction was extracted with HCl (10%). The combined organic phase was dried over $MgSO_4$ and concentrated. After removal of the solvent, a solid 7 (a- ... ) (depending on the phenylhydrazine derivative) was obtained.

Step 2

Compound 7 (1 eq) and $R_2H$ (1 eq) were dissolved in MeOH. The reaction mixture was stirred at room temperature for 12 h. A precipate of 8 was filtered off and washed with cold methanol.

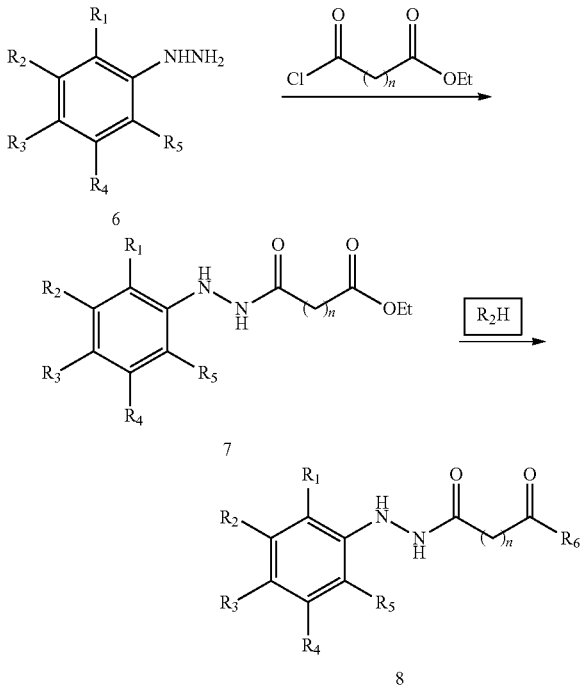

Bacterial Strains and Inoculum Preparation

Bacterial strains, from clinical origin, were supplied by the National Center for Microbiology, Institute of Health Carlos III (Majadahonda, Madrid). They are detailed in Table 1.

TABLE I

Characteristics of strains.

| Specie | Strain | Isolation year | IMP CTX A/C LIN AMK SxT CIP ERI PEN VAN RIF TET CLI MER CEF TOB GEN |
|---|---|---|---|
| *N. cyriacigeorgica* | 30 | 2005 | S S R S S S R R |
| *N. cyriacigeorgica* | 199 | 2005 | R R R S R S R R |
| *N. carnea* | 769 | 2009 | S S S S S R S R |
| *N. carnea* | 40 | 2011 | R S S R R S R |
| *T. pulmonis* | 1991 | 2009 | S S S S S S S S |
| *T. pulmonis* | 40 | 2015 | S R R R R R R R |
| *M. chelonae* | 870 | 2011 | R R R R R R |
| *M. abscessus* | 690 | 2012 | R S S R S R |
| *M. fortuitum* | 1080 | 2011 | R R S S R R |
| *B. cereus* | 25 | 2014 | R S S S R R |
| *B. cereus* | 182 | 2013 | R S S S S R |
| *A. baumannii* | 300 | 2001 | R R R R R S |
| *A. baumannii* | 1301 | 2009 | S S S S R S |
| *S. aureus* | 282 | 2005 | S R R S S R R |
| *S. aureus* | 890 | 2010 | S S R S R R R |
| *S. epidermidis* | 982 | 2006 | S R R S S R R |
| *S. epidermidis* | 188 | 2009 | S S S S S S S |
| *E. faecium* | 209 | 2015 | R R R S S |
| *E. faecium* | 26 | 2012 | R S R I S |
| *E. faecalis* | 1052 | 2008 | R S R S S |
| *E. faecalis* | 52 | 2006 | R S R S S |
| *P. aeruginosa* | 96 | 2014 | S S R S R S |

TABLE I-continued

Characteristics of strains.

| Specie | Strain | Isolation year | IMP | CTX | A/C | LIN | AMK | SxT | CIP | ERI | PEN | VAN | RIF | TET | CLI | MER | CEF | TOB | GEN |
|---|---|---|---|---|---|---|---|---|---|---|---|---|---|---|---|---|---|---|---|
| P. aeruginosa | 115 | 2013 | S | S | S | R | R | S |  |  |  |  |  |  |  |  |  |  |  |
| E. coli | 29 | 2012 | S | S | S | S | S | R | S |  |  |  |  |  |  |  |  |  |  |
| E. coli | 305 | 2008 | S | R | R | S | S | R | S |  |  |  |  |  |  |  |  |  |  |

IMP = Imipenem;
CTX = Cefotaxime;
A/C = Amoxicillin/Clavulanate;
Lin = Linezolid;
AMK = Amikacin;
SxT = Cotrimoxazole;
CIP = Ciprofloxacin;
ERI = Erythromycin;
PEN = Penicillin;
VAN = Vancomycin;
RIF = Rifampicin;
TET = Tetracycline;
CLI = Clindamycin;
MER = Meropenem;
CEF = Ceftriazone;
TOB = Tobramycin;
GEN = Gentamicin;
R = resistant,
S = susceptibility Antibacterial Susceptibility Test Bacterial cells suspension in sterile saline was prepared from a culture of 24-72 h, depending on bacterial species, in Mueller-Hinton Agar with 5% sheep blood. Each suspension was adjusted to a fixed size inoculum of $1-5\times10^8$ CFU/ml with a spectrophotometer (Ferraro, MJ National Committee for Clinical Laboratory Standards. 2000).

Kirby-Bauer disk diffusion susceptibility test protocol was utilized to determine the sensitivity or resistance of pathogenic bacteria against the compounds and others antibiotics. The absence of growth around the disks is an indirect measure of the ability of this compound to inhibit an organism (Kirby, W., et al., Antibiotics Annu. 1956-1957: 892). After 18 to 72 hours of incubation at 37° C., with or without $CO2$, under aerobic or anaerobic conditions, depending on the bacterial species, halo of growth inhibition were obtained and evaluated.

Antibiotic Activity

Interpretation of susceptibility and resistance was based on the presence or absence of a zone of inhibition surrounding the disk. Kirby-Bauer disk diffusion susceptibility test is a common method which uses antibiotic-impregnated wafers to test whether bacteria are affected by antibiotics. The size of the zone of inhibition depends on how effective the antibiotic is at stopping the growth of the bacterium. A stronger antibiotic will create a larger zone, because a lower concentration of the antibiotic is enough to stop growth.

Figure 1:
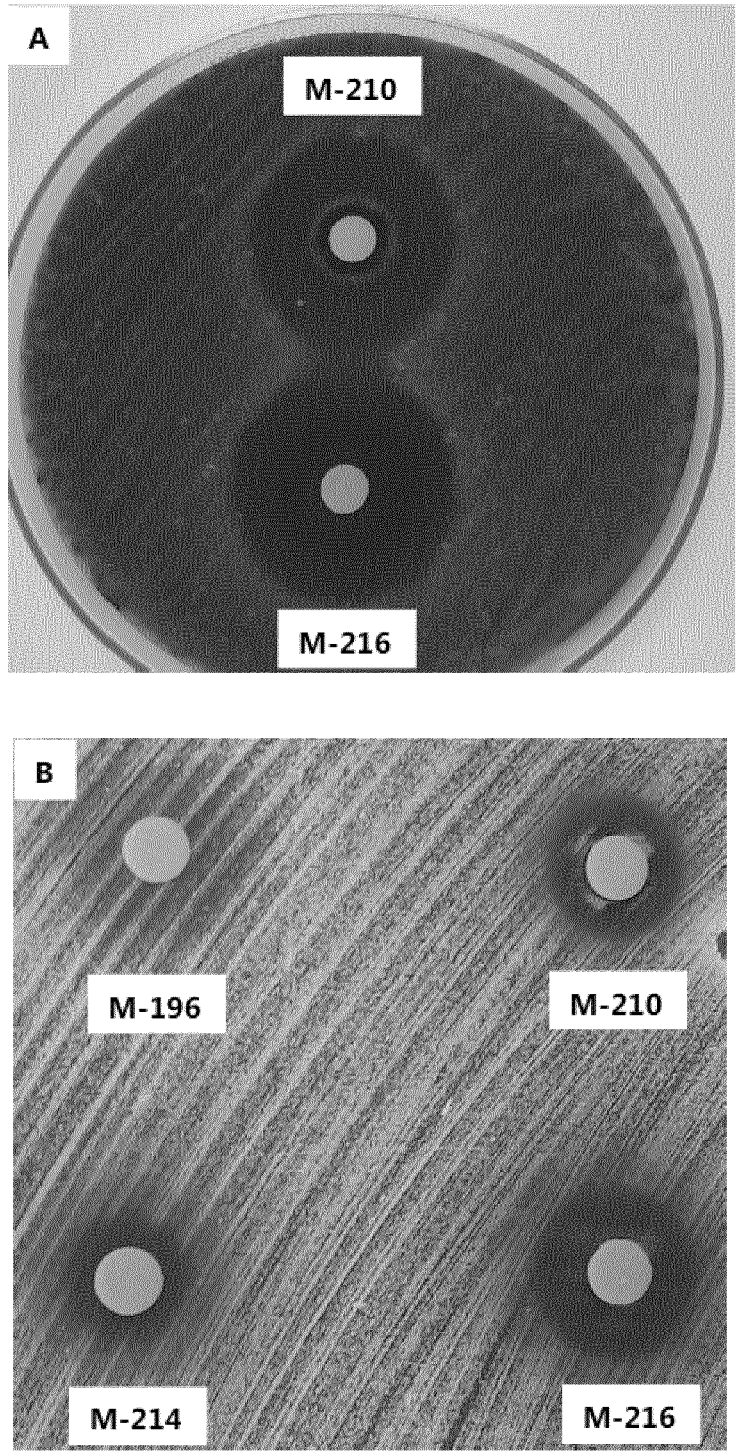
FIG. 1. Antibiotic activities detected with the compounds MSG-210 (M-210), MSG-216 (M-216), MSG-196 (M-196), MSG-214 (M-214), MSG-231 (M-231), MSG-235 (M-235). A: *T. pulmonis*: B: *N. carnea*; C: *S. pneumoniae*; D: *A. baumannii*; E: *T. pulmonis*; F: *N. cyriacigeorgica*; G: *E. faecalis*; H: *S. pneumoniae*; I: *A. baumannii*.
Figure 1:
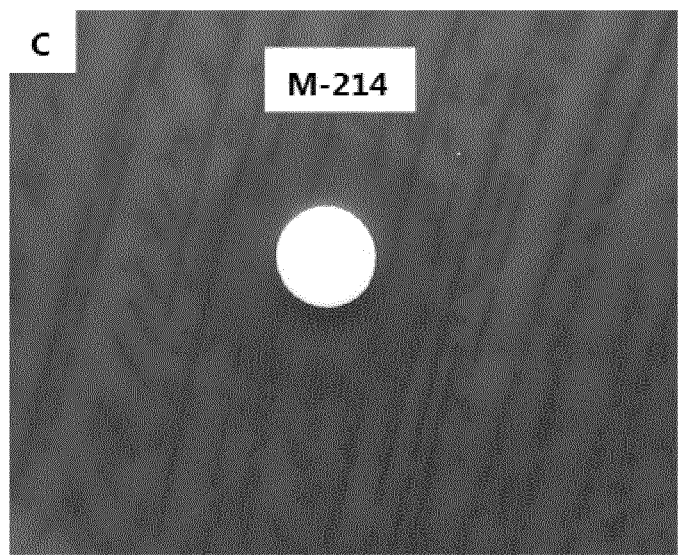
Figure 1:
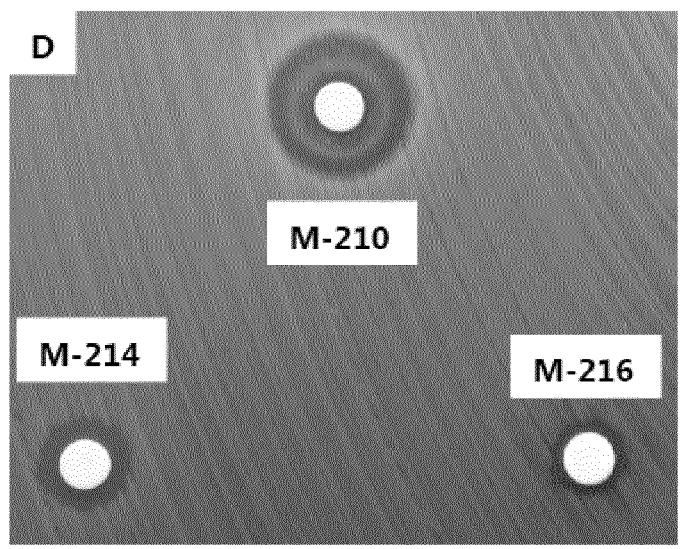
Figure 1:
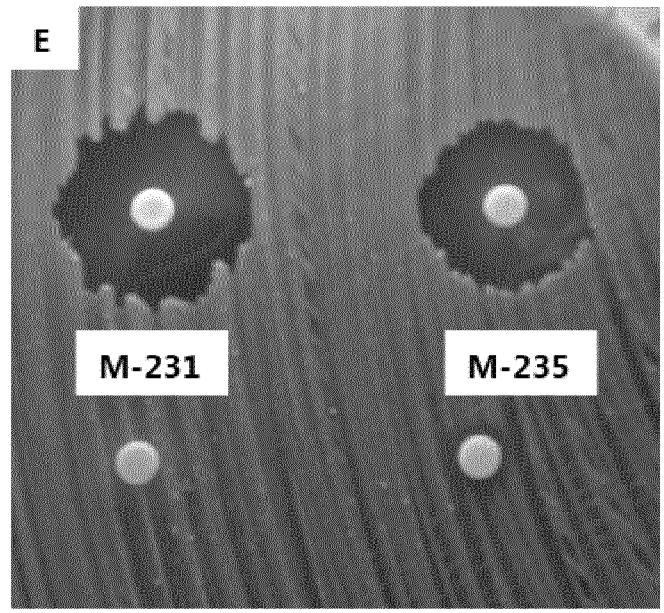
Figure 1:
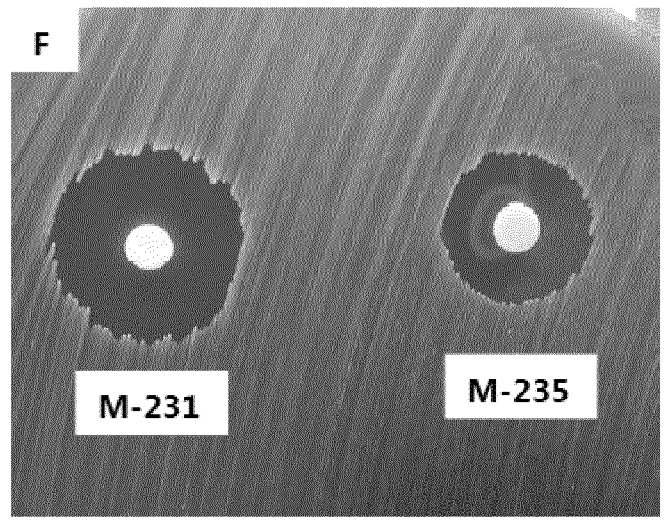
Figure 1:
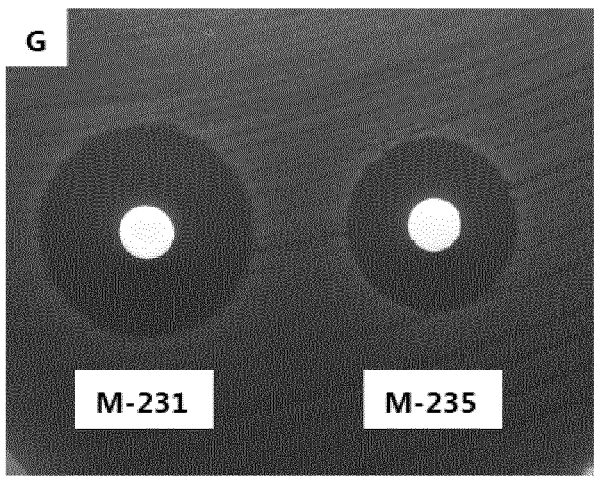
Figure 1:
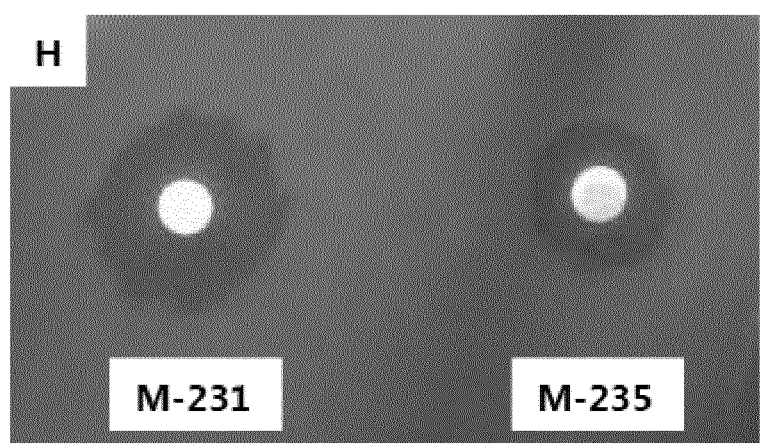
Figure 1:
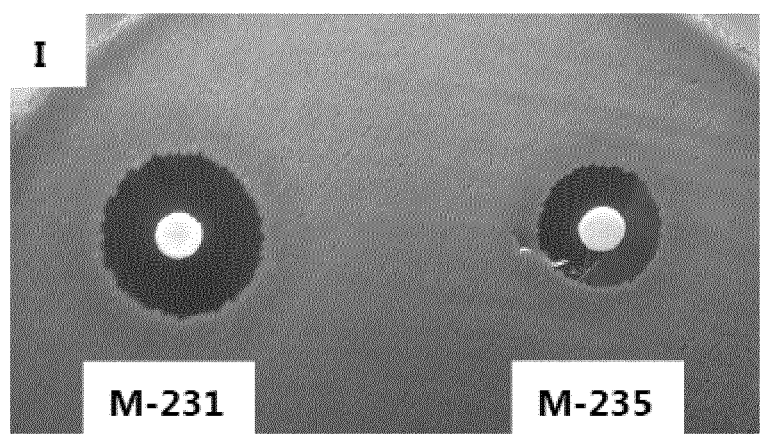
Figure 2:
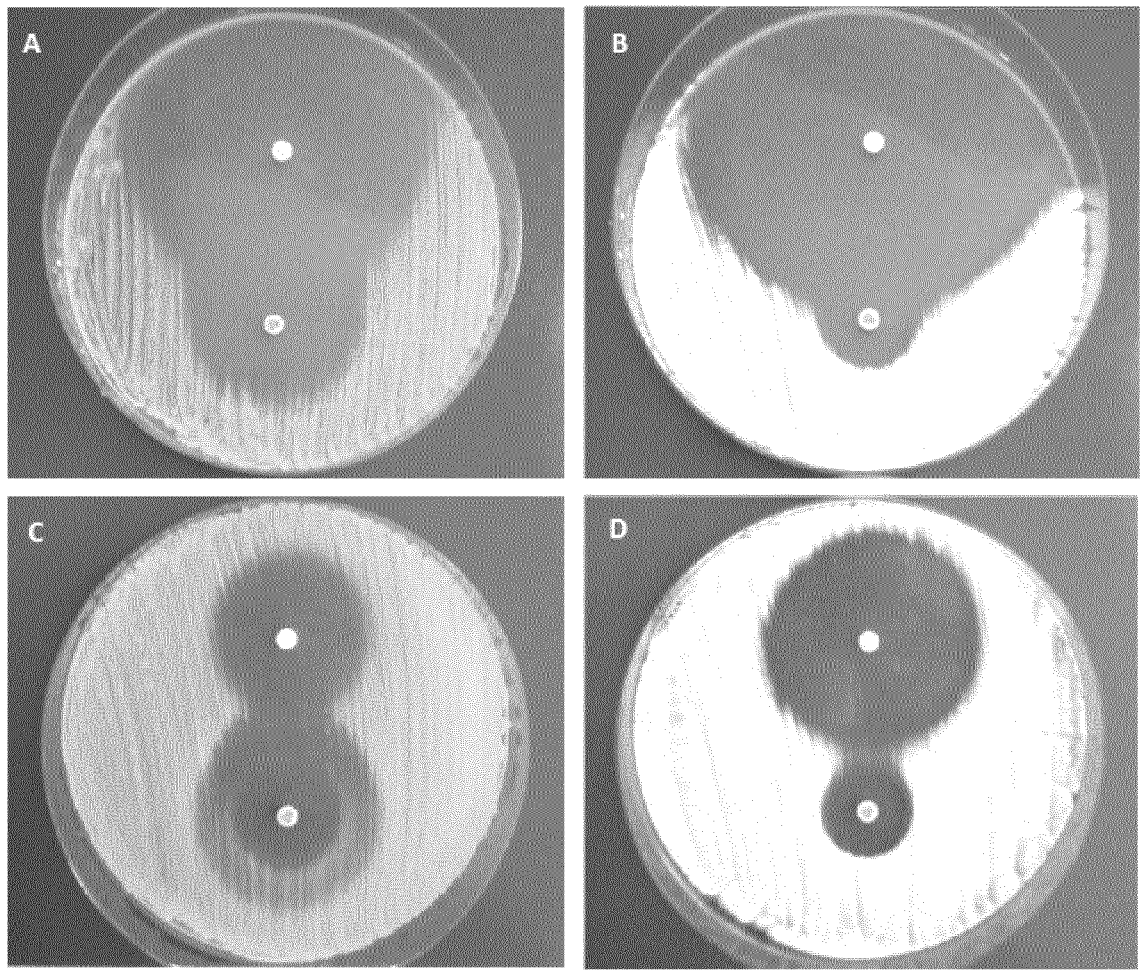
FIG. 2. Antifungal activity of the compound MSG-119. Compound MSG-119 500 μg in *C. albicans* (A) and *A.*

The results of antibiotic activity obtained with the Kirby-Bauer antibiotic test show the great potential of compounds, not only as molecules with specific activity against specific bacteria but also as possible structures for the development of broad spectrum antibiotics. The activity results are shown in Tables II-VIII and FIG. 1.

All compounds were tested at 300 µg/disc.

TABLE II

MSG-116

| Species | Activity detected (mm) 300 µg/disc MSG-196 |
|---|---|
| N. cyriacigeorgica | 34 |
| N. carnea | 30 |
| T. pulmonis | 22 |
| S. pneumoniae | 20 |
| S. pyogenes | 20 |
| K. pneumoniae | 13 |
| C. difficile | 18 |

TABLE III

MSG-210

| Species | Activity detected (mm) 300 µg/disc MSG-210 |
|---|---|
| N. cyriacigeorgica | 15 |
| N. carnea | 11 |
| T. pulmonis | 20 |
| A. baumannii | 18 |

TABLE IV

MSG-218

| Species | Activity detected (mm) MSG-218 |
|---|---|
| T. pulmonis | 33 |
| A. baumannii | 15 |

TABLE V

MSG-214

| Species | Activity detected (mm) 300 µg/disc MSG-214 |
|---|---|
| N. cyriacigeorgica | 25 |
| N. carnea | 14 |
| T. pulmonis | 30 |
| S. pneumoniae | 11 |
| A. baumannii | 12 |

TABLE VI

MSG-216

| Species | Activity detected (mm) 300 µg/disc MSG-216 |
|---|---|
| N. cyriacigeorgica | 17 |
| N. carnea | 14 |
| T. pulmonis | 25 |
| K. pneumoniae | 11 |
| A. baumannii | 12 |

TABLE VII

MSG-119

| Species | Activity detected (mm), 300 µg/disc MSG-419 |
|---|---|
| A. baumannii | 20 |
| P. aeruginosa | 15 |

TABLE VIII

MSG-213 and MSG-235

| | 300 µg | |
|---|---|---|
| Species | MSG-231 | MSG-235 |
| N. cyriacigeorgica | 33 | 29 |
| N. carnea | 38 | 34 |
| T. pulmonis | 27 | 24 |
| M. abscessus | 27 | 23 |
| C. difficile | 24 | 20 |
| E. faecium | 27 | 22 |
| E. foecalis | 29 | 25 |
| S. pneumoniae | 24 | 21 |
| S. epidermidis | 33 | 27 |
| K. pneumoniae | 10 | 12 |
| E. cloacae | 10 | 11 |
| A. baumannii | 20 | 15 |
| P. aeruginosa | 11 | 11 |
| E. coli | 17 | 14 |

Example 2-Antifungal Activity

Filamentous Fungi and Yeasts Strains and Inoculum Reparation

Filamentous fungi and yeasts strains, from clinical origin, were supplied by Microbiology Service from The Princess Hospital, Madrid. They are detailed in Table IX.

TABLE IX

Characteristics of the strains.

| yeast/fungus | Amphotericin B | Ketoconazole | Itraconazole | Clotrimazole | Fluconazole |
|---|---|---|---|---|---|
| C. albicans | I | S | R | S | S |
| C. glabrata | S | S | I | S | S |
| C. tropicalis | S | S | I | S | S |
| C. parapsilosis | S | S | S | S | S |
| C. lusitaniae | I | S | S | S | S |
| C. Krusei | I | S | R | S | S |
| C. guillermondii | R | R | R | R | R |
| A. fumigatus | S | S | I | S | R |
| A. niger | S | S | I | S | R |
| A. terreus | I | S | I | S | R |
| A. flavus | I | S | I | S | R |
| S. cerevisiae | I | S | S | R | S |

I = intermediate activity; S = susceptibility; R = Resistance

Filamentous fungi and yeast cells suspensions in distilled water was prepared from a culture of 24-48 h, depending on species, in Sabouraud agar. Each suspension was adjusted to a fixed size inoculum of $1-5 \times 10^8$ CFU/ml with a spectrophotometer (Ferraro, MJ National Committee for Clinical Laboratory Standards. 2000).

Antifungal Susceptibility Test

Antifungal susceptibility tests were developed following the standardized methodology detailed in document CLSI: M44-4: Method for Antifungal Disk diffusion susceptibility testing of yeasts consisting of disk diffusion on agar Muller-Hinton (supplemented with 2% glucose).

Antifungal Activity:

The activity results are shown in Table X. The compound was tested at 150 and 500 µg/disc. A great activity was exhibited in fungi strains and in *Candida* spp. (Table X and FIG. 2 to FIG. 8).

TABLE X

Antifungal activities detected with the compounds.

| | Activity (mm) | | | | | | | | | | | | | | | | | | | |
|---|---|---|---|---|---|---|---|---|---|---|---|---|---|---|---|---|---|---|---|---|
| Species | MSG-187 | | MSG-193 | | MSG-119 | | Ket | MSG-210 | | MSG-214 | | MSG-216 | | MSG-218 | | MSG-227 | | Clo |
| µg/disc | 150 | 500 | 150 | 500 | 150 | 500 | 50 µg | 150 | 500 | 150 | 500 | 150 | 500 | 150 | 500 | 150 | 500 | 10 µg |
| C. albicans | min | 22 | 20 | >40 | 21 | 24 | 22 | 32 | >40 | 40 | >40 | 24 | >40 | 24 | >40 | 26 | >40 | 15 |
| C. parapsilosis | min | 17 | 18 | >40 | 15 | >40 | 42 | 28 | 32 | 15 | >40 | 11 | >40 | 25 | 36 | 31 | >40 | 42 |
| C. lusitaniae | min | 20 | 15 | >40 | min | 20 | 41 | 39 | >40 | 42 | >40 | 36 | >40 | 22 | 46 | >40 | >40 | 41 |
| C. guillermondii | min | 22 | 20 | 40 | 12 | >40 | 44 | 32 | 35 | 15 | >40 | 13 | >40 | 22 | 40 | >40 | >40 | 44 |

TABLE X-continued

Antifungal activities detected with the compounds.

| Species | Activity (mm) | | | | | | | | | | | | | | | | | |
|---|---|---|---|---|---|---|---|---|---|---|---|---|---|---|---|---|---|---|
| | MSG-187 | | MSG-193 | | MSG-119 | | Ket | MSG-210 | | MSG-214 | | MSG-216 | | MSG-218 | | MSG-227 | | Clo |
| μg/disc | 150 | 500 | 150 | 500 | 150 | 500 | 50 μg | 150 | 500 | 150 | 500 | 150 | 500 | 150 | 500 | 150 | 500 | 10 μg |
| C. tropicalis | min | 18 | 30 | >40 | 20 | >40 | 25 | 34 | 36 | 34 | >40 | 26 | >40 | 10 | 40 | 26 | >40 | 25 |
| S. cerevisiae | min | min | 22 | 40 | 26 | 35 | 30 | 28 | 30 | 15 | 32 | 19 | 35 | 24 | 34 | 20 | 25 | 30 |
| A. niger | min | 40 | 15 | >40 | 24 | >40 | 25 | 27 | 40 | 10 | >40 | 10 | 36 | 22 | 30 | 32 | >40 | 25 |
| A. flavus | min | 36 | 15 | >40 | 18 | >40 | 32 | 10 | 9 | min | min | min | min | min | min | 25 | >40 | 32 |
| A. fumigatus | min | 32 | 20 | >40 | 22 | >40 | 22 | 10 | 16 | min | 16 | min | 10 | min | 10 | 11 | >40 | 22 |
| A. terreus | min | min | 12 | 32 | 20 | >40 | 26 | 19 | 22 | min | 17 | min | 10 | min | 10 | >40 | >40 | 26 |

Min: minimum detected activity (halo diameter <10 mm);
ket: ketoconazole;
Clo: clotrimazol

Example 3—Anti-HIV Activity

Antiviral Susceptibility Test

Assessment of in vitro antiviral activity is usually performed to estimate parameters of antiviral potency and efficacy represented by the percentage of inhibition of HIV activity or IC50. The assay utilized is based on the use of recombinant viruses in which the nef gene, essential for in vitro HIV replication, has been replaced by a *Renilla* reporter gene so that viral replication can be quantified directly (García-Perez J et al, J Med Virol. 2007 February; 79(2):127-37). The assay was performed infecting MT-2 cells or PHA-activated PBMCs/IL-2 with viral supernatants obtained previously. The study was development in AIDS Immunopathology Unit, Nacional Center of Microbiology, Institute of Health Carlos 111, Majadahonda, Madrid, Spain.

Viability

All assays for assessing anti-HIV activity were taken in parallel to determine cellular viability of the culture in the presence or absence of different concentrations of the isolated molecule. It was followed exactly the same methodology as in the anti-HIV assay except with the addition of complete DMEM medium instead of supernatant viral, in the same proportion, and the detection of the viability was performed with the viability detection kit CellTiter Glo (Promega), following manufacturer instructions. Viability is directly proportional to the luciferase activity obtained.

All data are expressed as percentage relative to a control with DMSO at the same concentration. Antiviral activity and toxicity curves were performed to the compound at different concentrations.

Results

The profile of activity/toxicity of the compounds was good with an intrinsic activity in the micromolar range medium (FIG. 9). The safety index value is more than 100 for all of them. As an example, IC50 value of MSG-119 is in the micromolar range (IC50 of 7, 11 μM) (Table XI).

TABLE XI

IC50 (half maximal inhibitory concentration) of the compound. 95% confidence interval (CI95%). CC50 means concentration of drug required to kill 50% of cells. The value R2 is a measure of goodness-of-fit of linear regression (using graphPad prism).

| | IC$_{50}$ VIH MT-2 μM | CI95% | R$^2$ | CC$_{50}$ VIH MT-2 μM | CI95% | R$^2$ |
|---|---|---|---|---|---|---|
| MSG-119 | 7.11 | 2.50 to 20.22 | 0.8604 | >100 | — | — |

Characterization of the Compounds

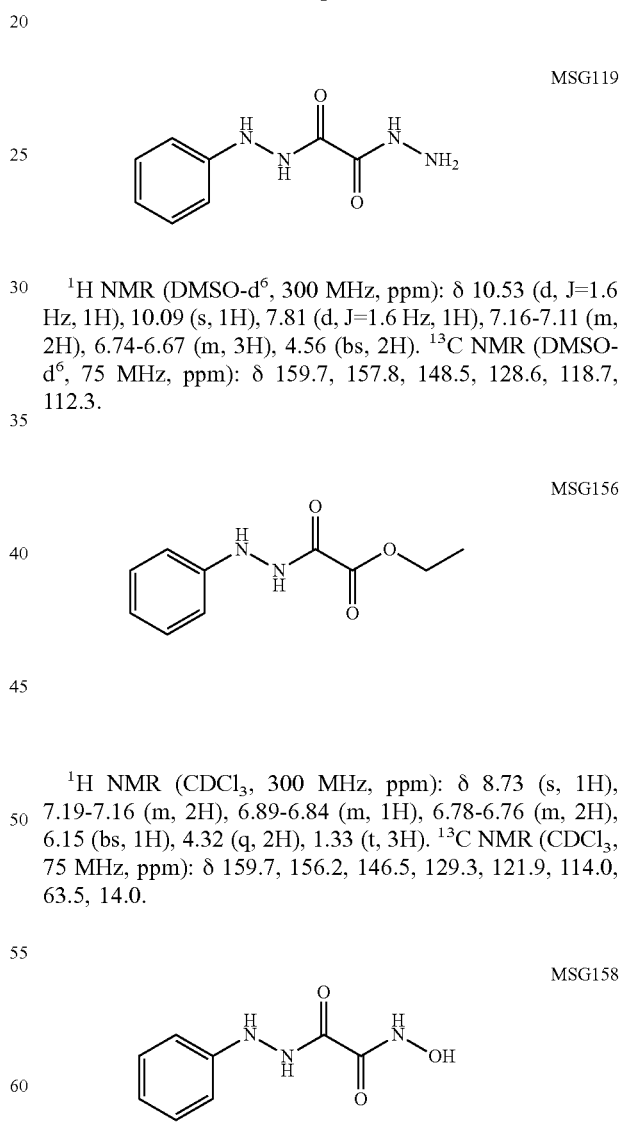

MSG119

$^1$H NMR (DMSO-d$^6$, 300 MHz, ppm): δ 10.53 (d, J=1.6 Hz, 1H), 10.09 (s, 1H), 7.81 (d, J=1.6 Hz, 1H), 7.16-7.11 (m, 2H), 6.74-6.67 (m, 3H), 4.56 (bs, 2H). $^{13}$C NMR (DMSO-d$^6$, 75 MHz, ppm): δ 159.7, 157.8, 148.5, 128.6, 118.7, 112.3.

MSG156

$^1$H NMR (CDCl$_3$, 300 MHz, ppm): δ 8.73 (s, 1H), 7.19-7.16 (m, 2H), 6.89-6.84 (m, 1H), 6.78-6.76 (m, 2H), 6.15 (bs, 1H), 4.32 (q, 2H), 1.33 (t, 3H). $^{13}$C NMR (CDCl$_3$, 75 MHz, ppm): δ 159.7, 156.2, 146.5, 129.3, 121.9, 114.0, 63.5, 14.0.

MSG158

$^1$H NMR (DMSO-d$^6$, 300 MHz, ppm): δ 11.56 (s, 1H), 10.55 (s, 1H), 9.25 (bs, 1H), 7.79 (bs, 1H), 7.16-7.12 (m, 2H), 6.74-6.68 (m, 3H). $^{13}$C NMR (DMSO-d$^6$, 75 MHz, ppm): δ 159.7, 157.8, 148.5, 128.6, 118.7, 112.3.

MSG159

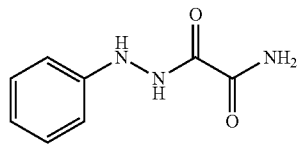

¹H NMR (DMSO-d⁶, 300 MHz, ppm): δ 10.50 (s, 1H), 8.10 (s, 1H), 7.83 (s, 1H), 7.78 (s, 1H), 7.17-7.12 (m, 2H), 6.74-6.69 (m, 3H). ¹³C NMR (DMSO-d⁶, 75 MHz, ppm): δ 161.9, 160.2, 148.5, 128.6, 118.8, 112.3.

MSG160

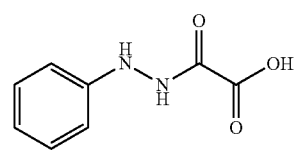

¹H NMR (DMSO-d⁶, 300 MHz, ppm): δ 10.60 (s, 1H), 7.18-7.13 (m, 2H), 6.75-6.71 (m, 3H). ¹³C NMR (DMSO-d⁶, 75 MHz, ppm): δ 161.9, 158.6, 148.4, 128.7, 118.9, 112.4.

MSG.161

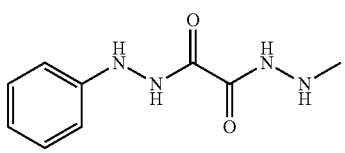

¹H NMR (DMSO-d⁶, 300 MHz, ppm): δ 10.33 (s, 1H), 7.82 (s, 1H), 7.18-7.12 (m, 2H), 6.75-6.68 (m, 3H), 2.51 (s, 3H). ¹³C NMR (DMSO-d⁶, 75 MHz, ppm): δ 159.9, 157.4, 148.4, 128.8, 118.9, 112.4, 38.0.

MSG187

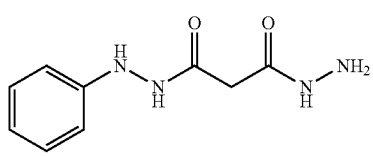

¹H NMR (DMSO-d⁶, 300 MHz, ppm): δ 9.67 (s, 1H), 9.13 (s, 1H), 7.72 (s, 1H), 7.14-7.09 (m, 2H), 6.76-6.68 (m, 3H), 4.26 (s, 1H), 3.04 (s, 2H). ¹³C NMR (DMSO-d⁶, 75 MHz, ppm): δ 166.4, 165.8.4, 149.0, 128.5, 118.4, 112.1, 40.2

MSG193

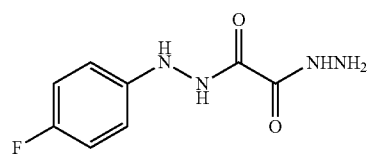

¹H NMR (DMSO-d⁶, 300 MHz, ppm): δ 10.56 (bs, 1H), 10.08 (bs, 1H), 7.78 (s, 1H), 6.98 (d, J=7.0 Hz, 2H), 6.70 (d, J=7.0 Hz, 2H), 4.56 (s, 2H). ¹³C NMR (DMSO-d⁶, 75 MHz, ppm): δ 160.2, 158.2, 156.4 (d, J=234 Hz), 145.5, 115.5 (d, J=22 Hz), 114.1 (d, J=7.5 Hz)

MSG.196

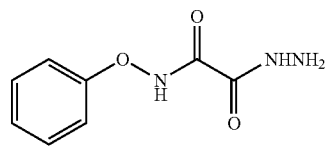

¹H NMR (DMSO-d⁶, 300 MHz, ppm): 7.19 (t, J=7.8, 1H), 7.09 (d, J=8.0 Hz, 2H), 6.80 (d, J=7.2 Hz, 2H). ¹³C NMR (DMSO-d⁶, 75 MHz, ppm): δ 159.9, 157.4, 148.4, 128.8, 118.9, 112.4

MSG210

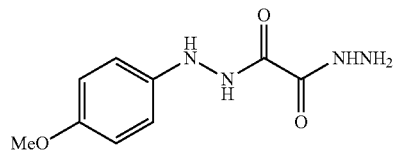

¹H NMR (DMSO-d⁶, 300 MHz, ppm): δ 10.48 (s, 1H), 10.05 (s, 1H), 7.48 (s, 1H), 6.75-6.69 (m, 4H), 4.54 (s, 2H), 3.66 (s, 3H). ¹³C NMR (DMSO-d⁶, 75 MHz, ppm): δ 166.4, 165.8, 149.0, 128.5, 118.4, 112.1, 40.2

MSG214

¹H NMR (DMSO-d⁶, 300 MHz, ppm): δ 10.60 (s, 1H). 10.10 (s, 1H), 8.00 (s, 1H), 7.17 (d, J=8.7 Hz, 2H), 6.69 (d, J=8.7 Hz, 2H), 4.55 (s, 2H). ¹³C NMR (DMSO-d⁶, 75 MHz, ppm): δ 159.7, 157.6, 147.5, 128.4, 122.0, 113.8.

MSG216

¹H NMR (DMSO-d⁶, 300 MHz, ppm): δ 10.60 (s, 1H), 10.11 (s, 1H), 8.02 (s, 1H), 7.29 (d, J=8.5 Hz, 2H), 6.64 (d, J=8.5 Hz, 2H), 4.55 (s, 2H). ¹³C NMR (DMSO-d, 75 MHz, ppm): δ 159.7, 157.6, 147.9, 131.3, 114.2, 109.5.

MSG218

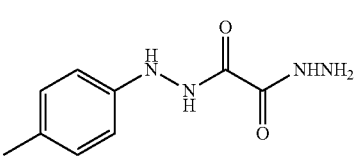

$^1$H NMR (DMSO-d$^6$, 300 MHz, ppm): δ 10.45 (bs, 1H), 10.06 (bs, 1H), 7.62 (s, 1H), 6.95 (d, J=7.8 Hz, 2H), 6.61 (d, J=7.8 Hz, 2H), 4.55 (s, 2H), 2.17 (s, 3H). $^{13}$C NMR (DMSO-d$^6$, 75 MHz, ppm): δ 159.6, 157.8, 146.2, 129.0, 127.4, 112.6, 20.1.

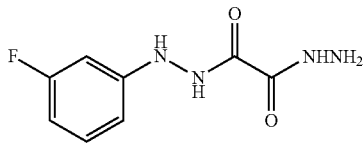

MSG227

$^1$H NMR (DMSO-d$^6$, 300 MHz, ppm): δ 10.60 (bs, 1H), 10.12 (bs, 1H), 8.13 (s, 1H), 7.19-7.11 (m, 1H), 6.53-6.39 (m, 3H), 4.55 (s, 2H). $^{13}$C NMR (DMSO-d$^6$, 75 MHz, ppm): δ 163.0 (d, J=242 Hz), 159.7, 157.6, 130.3 (d, J=10.2 Hz), 108.2, 104.7 (d, J=22 Hz), 98.7 (d, J=26.8 Hz).

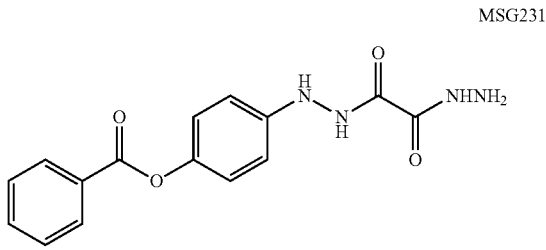 [SMILES: NNC(=O)C(=O)NNc1ccc(OC(=O)c2ccccc2)cc1]

MSG231

$^1$H NMR (DMSO-d$^6$, 300 MHz, ppm): δ 10.61 (bs, 1H), 10.11 (bs, 1H), 8.12-8.09 (m, 2H), 7.93 (s, 1H), 7.76-7.71 (m, 1H), 7.62-7.57 (m, 2H), 7.05 (d, J=8.1 Hz, 2H), 6.75 (d, J=8.1 Hz, 2H), 4.56 (s, 2H). $^{13}$C NMR (DMSO-d$^6$, 75 MHz, ppm): δ 165.0, 159.8, 157.8, 146.5, 143.0, 133.8, 129.6, 128.9, 121.9, 112.8.

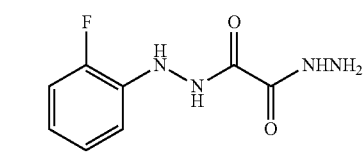

MSG235

$^1$H NMR (DMSO-d$^6$, 300 MHz, ppm): δ 10.6 (bs, 1H), 10.11 (bs, 1H), 7.75 (s, 1H), 7.11-6.96 (m, 2H), 6.73-6.67 (m, 2H), 4.56 (s, 2H). $^{13}$C NMR (DMSO-d$^6$, 75 MHz, ppm): δ 159.8, 157.6, 150.2 (d, J=239.5 Hz), 136.1 (d, J=9.8 Hz), 124.5 (d, J=3 Hz), 118.9 (d, J=7 Hz), 114.8 (d, J=18 Hz), 113.6 (d, J=3 Hz).

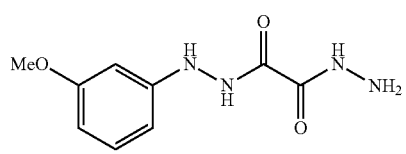

MSG.237

$^1$H NMR (DMSO-d$^6$, 300 MHz, ppm): δ 10.5 (bs, 1H), 10.08 (bs, 1H), 7.81 (s, 1H), 7.06-7.01 (m, 1H), 6.31-6.24 (m, 3H), 4.57 (s, 2H), 3.67 (s, 3H). $^{13}$C NMR (DMSO-d$^6$, 75 MHz, ppm): δ 160.5, 160.2, 158.2, 150.4, 130.0, 105.6, 104.6, 98.7, 55.2

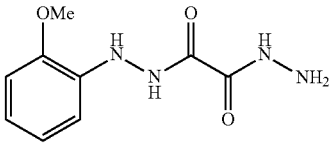

MSG.239

$^1$H NMR (DMSO-d$^6$, 300 MHz, ppm): δ 10.6 (bs, 1H), 10.08 (bs, 1H), 7.03 (s, 1H), 6.88-6.61 (m, 4H), 4.56 (s, 2H), 3.81 (s, 3H). $^{13}$C NMR (DMSO-d$^6$, 75 MHz, ppm): δ 159.4, 157.6, 146.5, 137.3, 120.6, 119.3, 111.6, 110.5, 55.5

The invention claimed is:

1. A compound of formula (I):

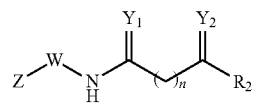

(I)

or a pharmaceutically acceptable salt, stereoisomer or solvate thereof, wherein

Y$_1$=O;

Y$_2$=O;

W=NH;

n=0, 1;

R$_2$=NHR$_4$, wherein R$_4$ is selected from the group consisting of OH, —NH$_2$, —NH—CH$_3$ and —NR$_a$Rb, wherein R$_a$ and Rb are independently selected C$_{1-6}$ alkyl groups or aryl groups;

Z=1-pyridine, 2-pyridine, 3-pyridine or phenyl, wherein the phenyl is optionally substituted with one or more groups independently selected from the group consisting of C$_{1-6}$ alkyl, C$_{2-6}$ alkenyl, halogen, —SH, —OR$_5$, —SR$_5$, OH, NO$_2$, C(O)NH—R$_5$, —C(O)OR$_5$, —OC(O)R$_5$, CF$_3$, CN, —NH$_2$, NHOH, —NH—NH$_2$, —NH—CH$_3$ and —NR$_6$R$_7$, wherein R$_5$ is C$_{1-6}$ alkyl, aryl or hydrogen, wherein R$_6$ and R$_7$ are independently C$_{1-6}$ alkyl, aryl, —C(O) R$_5$, —OC(O)R$_5$, or —C(O) OR$_5$, with the proviso that when Y$_1$=Y$_2$=O, n=0 R$_2$=NHNH$_2$ and W is NH then Z is not a group selected from the group consisting of a pyridine group, and a phenyl group wherein the phenyl group is optionally substituted with methyl, halogen, NO$_2$ or OCH$_3$ group, and wherein the compound is other than

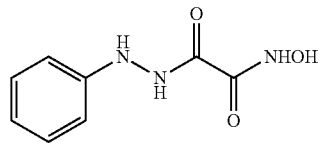

and other than

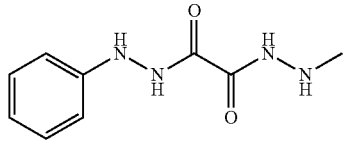

2. The compound as defined in claim 1, wherein $R_2$ is $NHNH_2$ and/or wherein n is 1 and $Y_1=Y_2=O$.

3. The compound as defined in claim 1, wherein Z is a phenyl group optionally substituted with one or more groups independently selected from the group consisting of $C_{1-8}$ alkyl, $C_{2-8}$ alkenyl, halogen, —SH, —$OR_5$, —$SR_5$, —OH, —$NO_2$, —C(O)NH—$R_5$, —C(O)$OR_5$, —OC(O)$R_5$, —$CF_3$, —CN, —$NH_2$, —NHOH, —$NHNH_2$, —NH—$CH_3$ and —$NR_6R_7$, wherein $R_5$ is $C_{1-6}$ alkyl, aryl or hydrogen and wherein $R_6$ and $R_7$ are independently $C_{1-6}$ alkyl groups, aryl groups, —C(O) $R_5$, —OC(O)$R_5$, or —C(O)$OR_5$.

4. The compound as defined in claim 1, having (Ia) MSG187

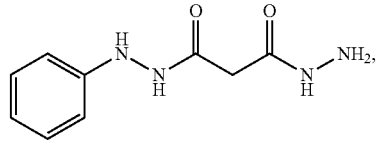

(If) MSG196

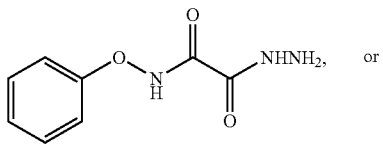 or (Ig) MSG231

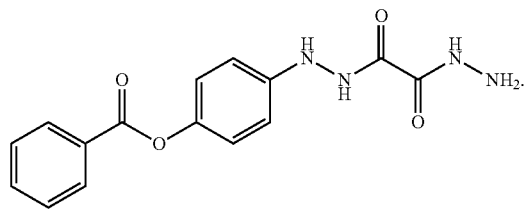

* * * * *